(12) United States Patent
Scalici et al.

(10) Patent No.: US 9,907,505 B2
(45) Date of Patent: Mar. 6, 2018

(54) METHODS AND DEVICES FOR DETECTING BOWEL PERFORATION

(75) Inventors: Tony Scalici, Delray Beach, FL (US); David Leonard, Madison, AL (US); David Krasne, New York, NY (US); Balakrishna Haridas, Mason, OH (US); M. Robert Garfield, III, Cincinnati, OH (US)

(73) Assignee: Sentire Medical Systems, LLC, New York, NY (US)

( * ) Notice: Subject to any disclaimer, the term of this patent is extended or adjusted under 35 U.S.C. 154(b) by 1158 days.

(21) Appl. No.: 13/442,266

(22) Filed: Apr. 9, 2012

(65) Prior Publication Data

US 2013/0096399 A1 Apr. 18, 2013

Related U.S. Application Data

(60) Provisional application No. 61/473,592, filed on Apr. 8, 2011.

(51) Int. Cl.
*A61B 5/00* (2006.01)
*A61M 31/00* (2006.01)
*B01D 39/00* (2006.01)
*A61B 17/34* (2006.01)
*G01N 21/3504* (2014.01)
*A61M 13/00* (2006.01)

(52) U.S. Cl.
CPC .......... *A61B 5/4255* (2013.01); *A61B 5/0002* (2013.01); *A61B 17/3474* (2013.01); *B01D 39/00* (2013.01); *A61B 2505/05* (2013.01); *A61M 13/003* (2013.01); *G01N 21/3504* (2013.01)

(58) Field of Classification Search
CPC ....................................................... A61B 5/00
USPC ............ 600/309, 560, 561; 96/134; 210/266
See application file for complete search history.

(56) References Cited

U.S. PATENT DOCUMENTS

| | | | | |
|---|---|---|---|---|
| 4,366,054 | A * | 12/1982 | Kronsbein | B01D 39/16 210/266 |
| 4,525,182 | A * | 6/1985 | Rising | A61M 5/165 210/436 |
| 4,559,066 | A * | 12/1985 | Hunter | B01D 46/0004 55/498 |
| 5,169,528 | A * | 12/1992 | Karbachsch | B01D 24/008 210/264 |
| 5,360,396 | A * | 11/1994 | Chan | A61M 13/003 600/560 |

(Continued)

FOREIGN PATENT DOCUMENTS

WO WO2010/042204 4/2010

OTHER PUBLICATIONS

European Search Report 12768238.5 dated Sep. 2014.
(Continued)

*Primary Examiner* — May Abouelela
(74) *Attorney, Agent, or Firm* — Mintz, Levin, Cohn, Ferris, Glovsky & Popeo P.C.

(57) ABSTRACT

The present disclosure relates to methods and devices to detect perforation of the bowel, for example, resulting from surgical procedures, such as laparoscopy, diagnostic procedures, such as colonoscopy, medical conditions, such as diverticulitis, and trauma. The present disclosure also relates to filtration systems and electrical connector assemblies for use in the methods and devices.

11 Claims, 34 Drawing Sheets

(56) References Cited

U.S. PATENT DOCUMENTS

| | | | | |
|---|---|---|---|---|
| 5,411,474 | A * | 5/1995 | Ott | A61M 13/003 600/560 |
| 5,874,052 | A * | 2/1999 | Holland | B01D 46/12 422/122 |
| 6,206,878 | B1 * | 3/2001 | Bishop | A61B 18/042 219/121.55 |
| 6,299,592 | B1 * | 10/2001 | Zander | A61M 13/003 600/560 |
| 6,379,437 | B1 * | 4/2002 | Heinonen | B01D 53/02 55/521 |
| 6,402,714 | B1 * | 6/2002 | Kraft-Kivikoski | A61M 13/003 600/560 |
| 6,524,307 | B1 * | 2/2003 | Palmerton | A61B 18/00 604/22 |
| 6,645,197 | B2 * | 11/2003 | Garrison | A61B 17/00234 600/560 |
| 6,896,713 | B1 | 5/2005 | Eckerbom et al. | |
| 6,955,761 | B2 * | 10/2005 | France | B01D 39/00 210/264 |
| 7,217,351 | B2 * | 5/2007 | Krumme | A61K 9/0024 204/600 |
| 8,186,347 | B2 * | 5/2012 | Haggblom | A61M 16/01 128/205.12 |
| 8,414,550 | B2 * | 4/2013 | Roberts | A61B 17/3474 128/207.14 |
| 8,758,625 | B2 * | 6/2014 | Kato | B01D 61/147 210/500.23 |
| 2002/0043493 | A1 | 4/2002 | Patil | |
| 2002/0099319 | A1 * | 7/2002 | Saito | A61M 1/3693 604/6.04 |
| 2004/0019312 | A1 * | 1/2004 | Childers | A61M 1/1656 604/4.01 |
| 2004/0048392 | A1 * | 3/2004 | Kidd | B01L 3/50853 436/178 |
| 2004/0050791 | A1 * | 3/2004 | Herczeg | B01D 61/145 210/651 |
| 2005/0005936 | A1 * | 1/2005 | Wondka | A61M 16/04 128/204.18 |
| 2005/0067340 | A1 | 3/2005 | Broens et al. | |
| 2005/0211934 | A1 * | 9/2005 | Garber | B67D 7/348 251/129.01 |
| 2006/0129087 | A1 * | 6/2006 | Uesugi | A61M 13/003 604/26 |
| 2007/0000300 | A1 | 1/2007 | Diemunsch et al. | |
| 2007/0021808 | A1 * | 1/2007 | Rojas | A61F 7/0085 607/105 |
| 2007/0246419 | A1 * | 10/2007 | Milosavljevic | B01D 46/0023 210/284 |
| 2007/0282219 | A1 * | 12/2007 | Holte | A61B 5/036 600/561 |
| 2008/0082084 | A1 * | 4/2008 | Roberts | A61B 17/3474 604/540 |
| 2008/0087108 | A1 * | 4/2008 | Kreikebaum | G01N 1/2202 73/863.23 |
| 2008/0265191 | A1 | 10/2008 | Walborn | |
| 2008/0283062 | A1 | 11/2008 | Esposito, Jr. | |
| 2009/0000475 | A1 | 1/2009 | Fekety et al. | |
| 2009/0093734 | A1 * | 4/2009 | Stevenson | A61M 5/1452 600/560 |
| 2009/0189102 | A1 * | 7/2009 | Linden | F16K 17/38 251/129.01 |
| 2010/0089121 | A1 * | 4/2010 | Hemmingsson | G01N 33/497 73/23.3 |
| 2010/0107878 | A1 * | 5/2010 | Crowder | B01D 19/0031 96/6 |
| 2010/0185139 | A1 | 7/2010 | Stearns et al. | |
| 2010/0228100 | A1 * | 9/2010 | Vining | A61B 5/036 600/300 |
| 2010/0330603 | A1 * | 12/2010 | Zhu | G01N 1/2205 435/29 |
| 2011/0181427 | A1 * | 7/2011 | Matsubara | G08B 21/18 340/632 |
| 2014/0275868 | A1 * | 9/2014 | Rule | A61B 5/0002 600/310 |

OTHER PUBLICATIONS

International Search Report of PCT/US2012/032705 dated Dec. 14, 2012.
Communication pursuant to Article 94(3) EPC dated Nov. 21, 2016, from EP Application No. 12768238.3.

* cited by examiner

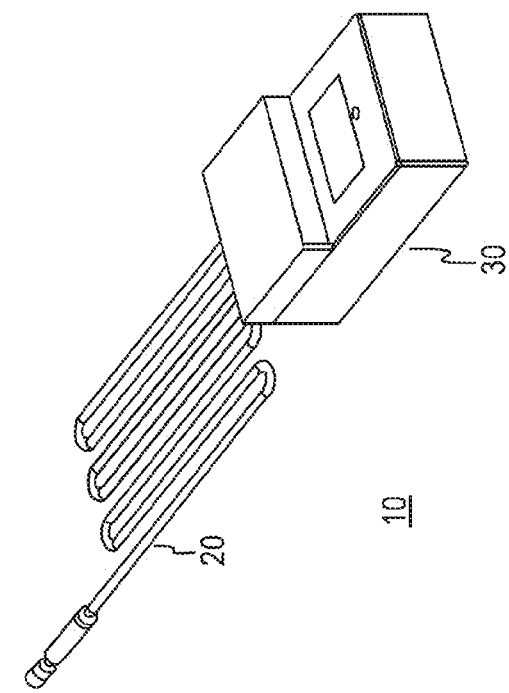
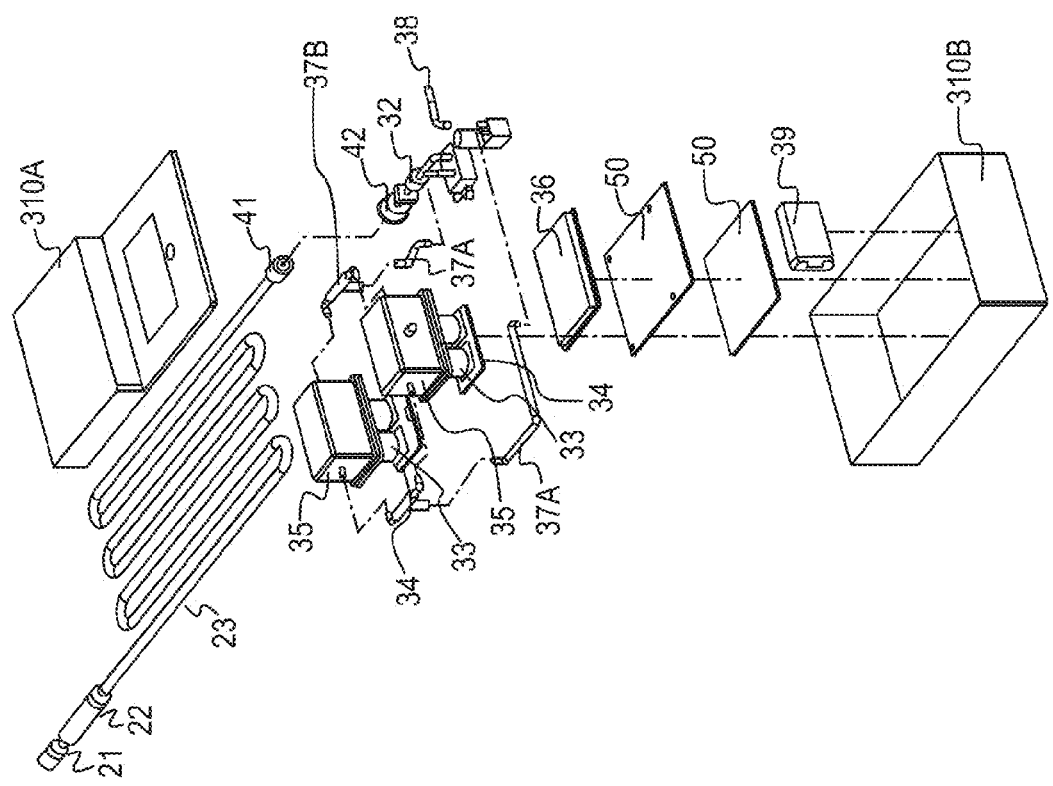
FIG. 1B

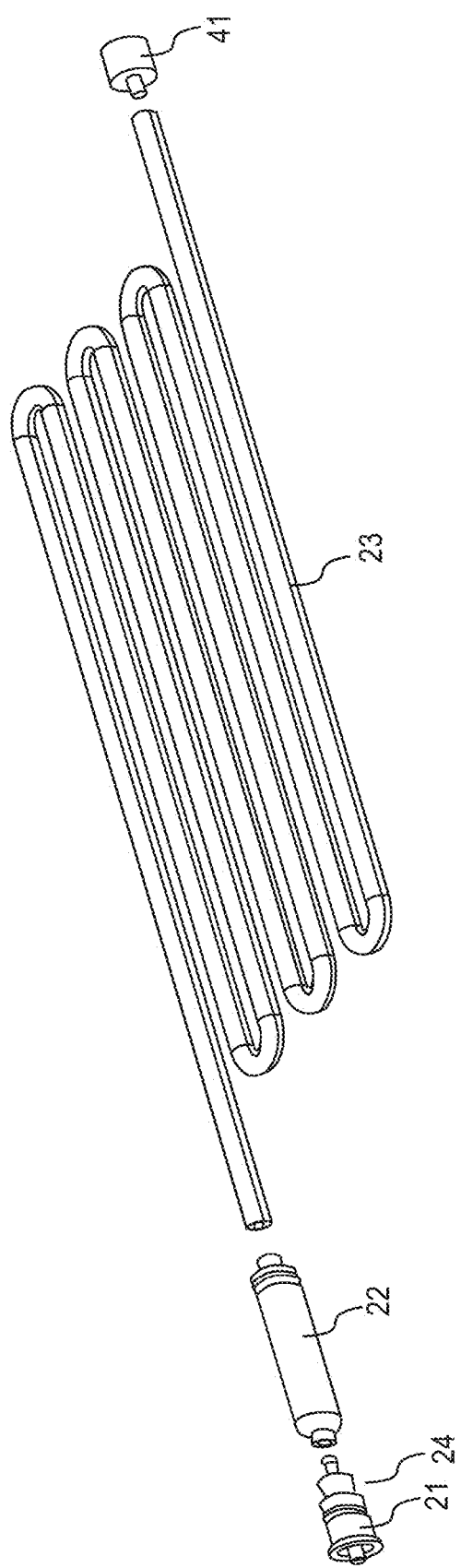

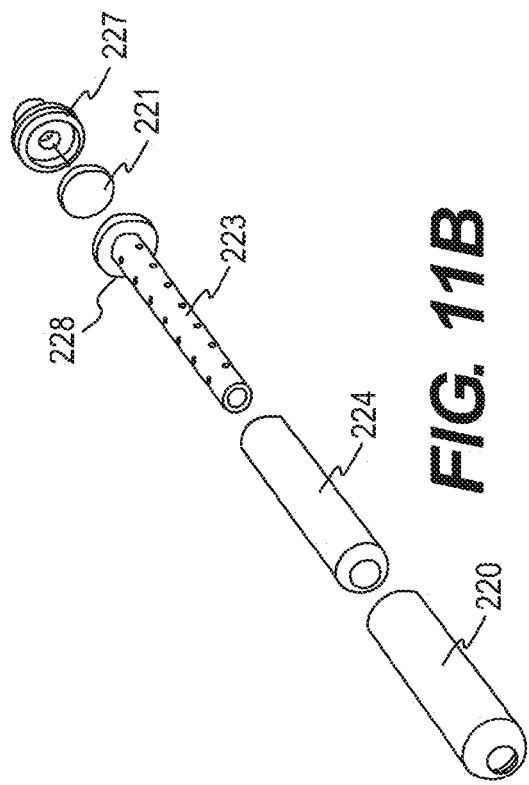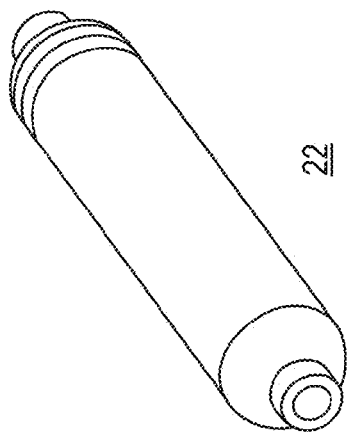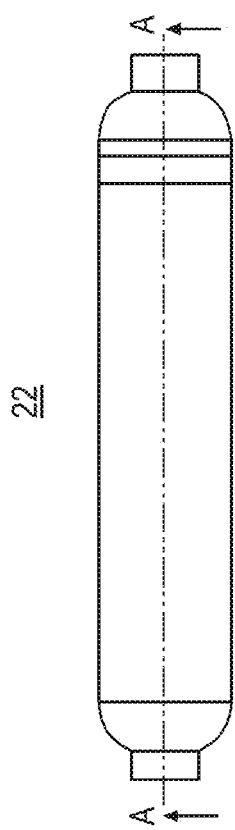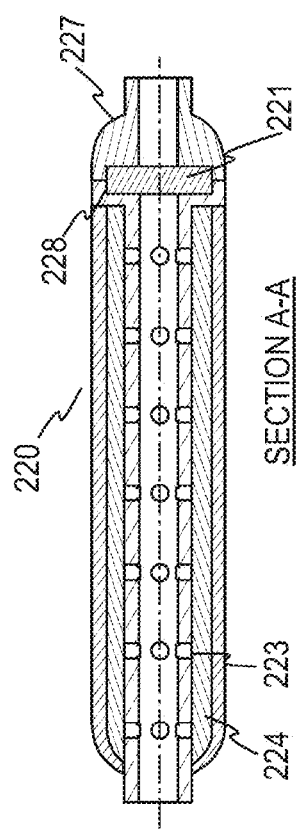
FIG. 11A
FIG. 11B
FIG. 11C
FIG. 11D SECTION A-A

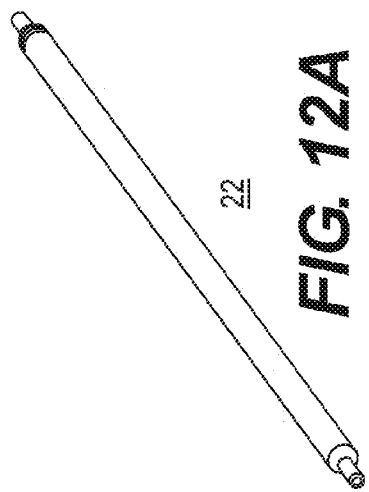
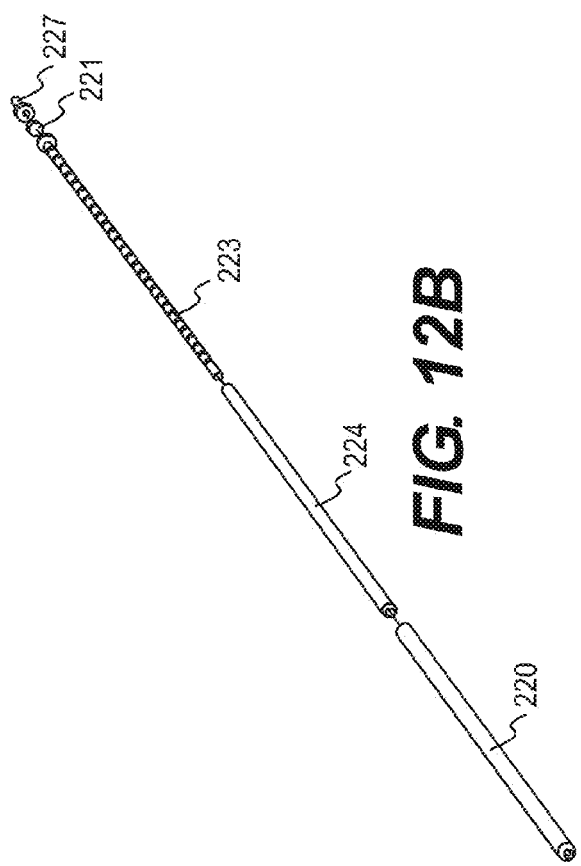
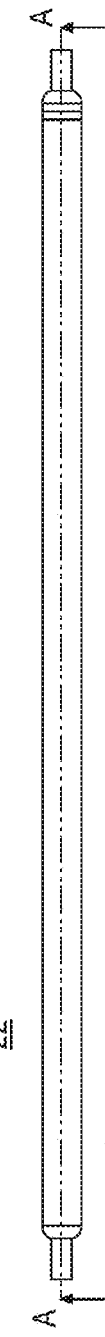
FIG. 12A
FIG. 12B
FIG. 12C
FIG. 12D
SECTION A-A

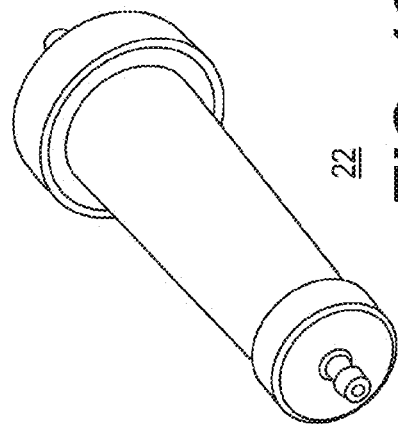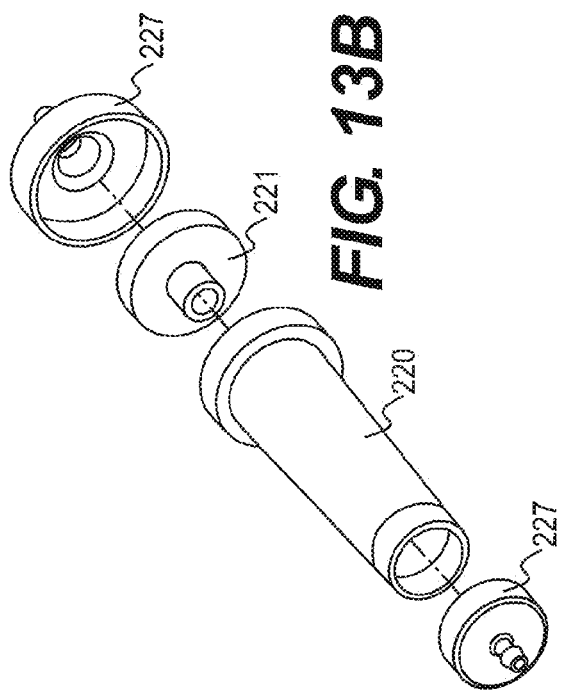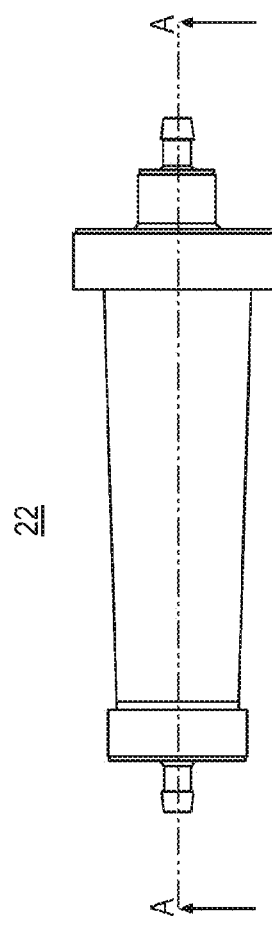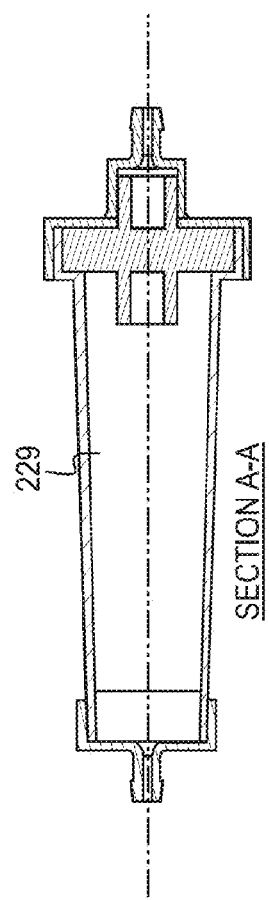

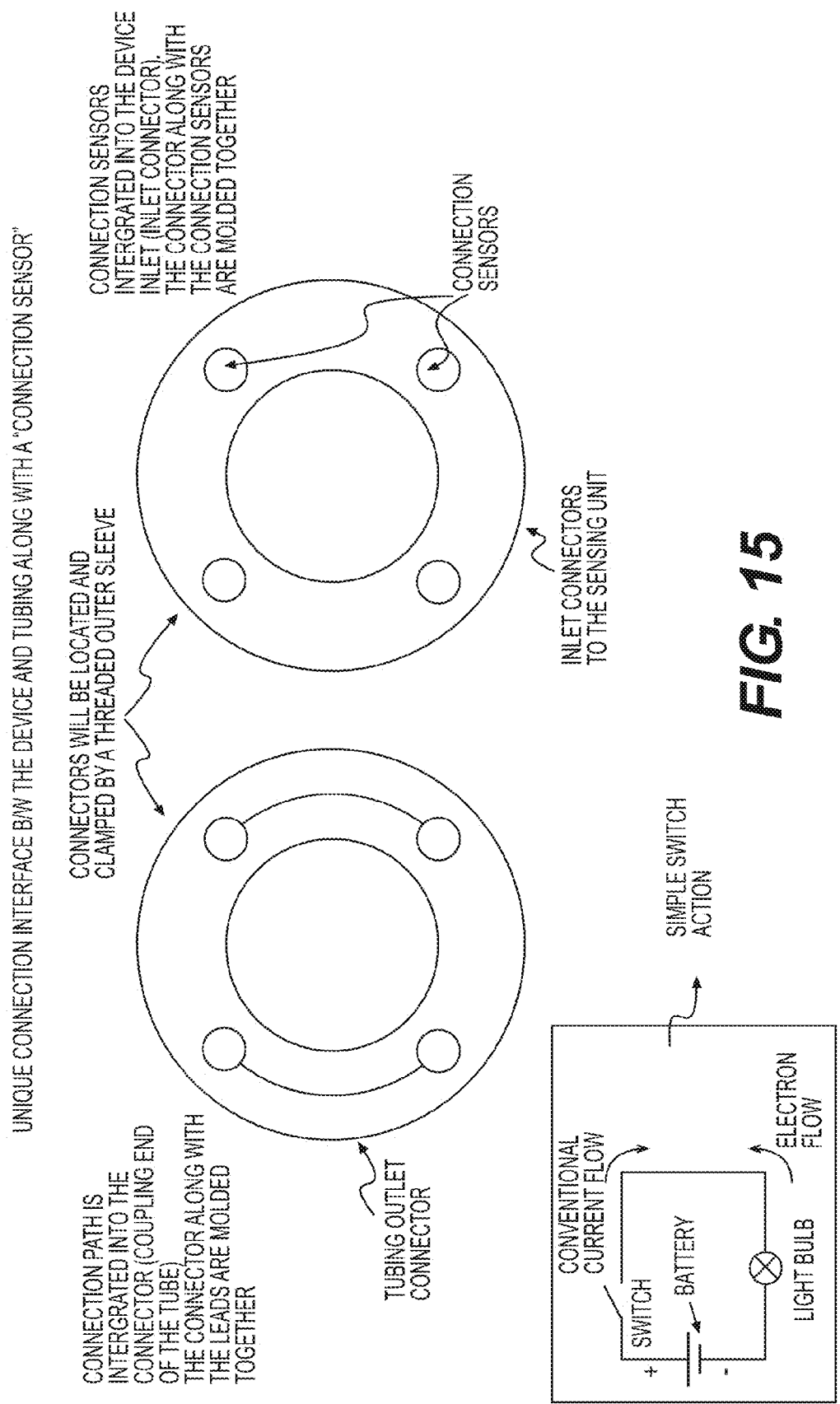

ARCHITECTURE-1 AND 2 (SEQUENTIAL AND SERIES SENSING)

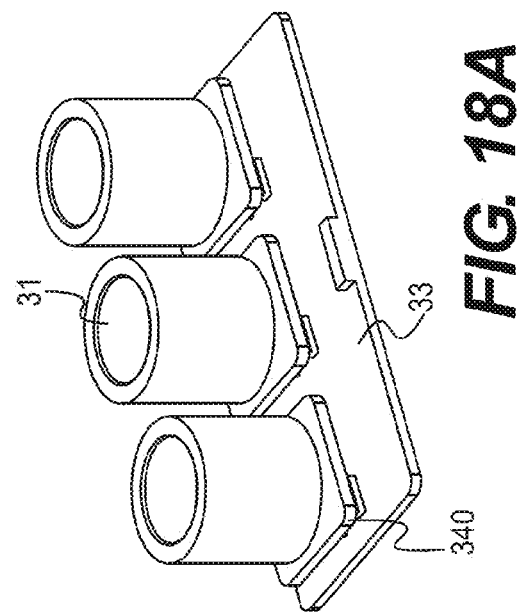
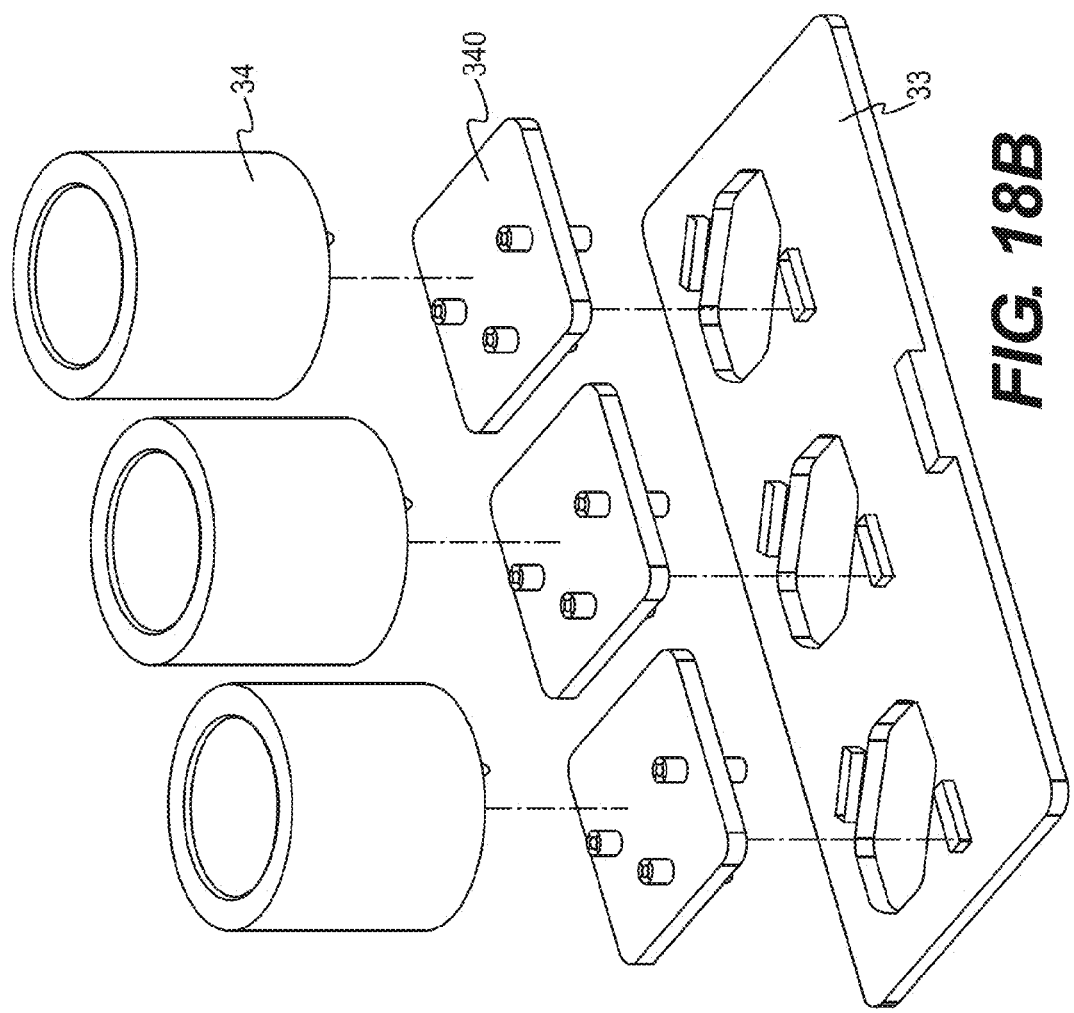

SECTION A-A

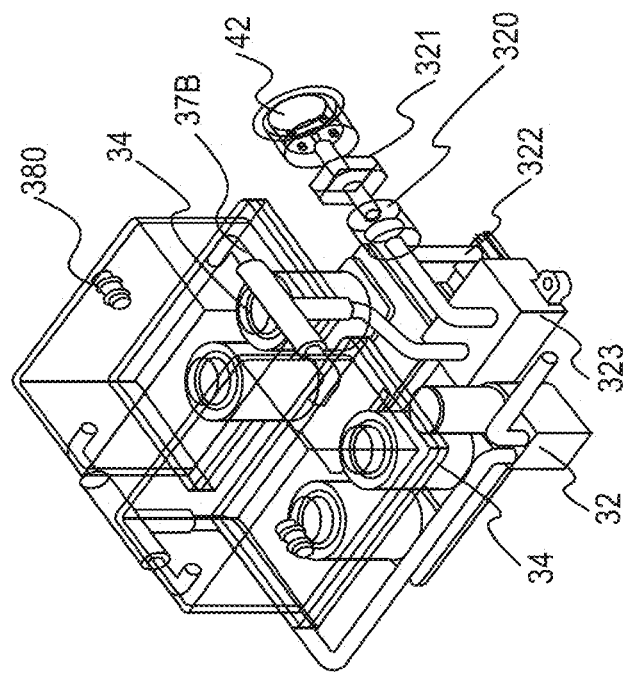
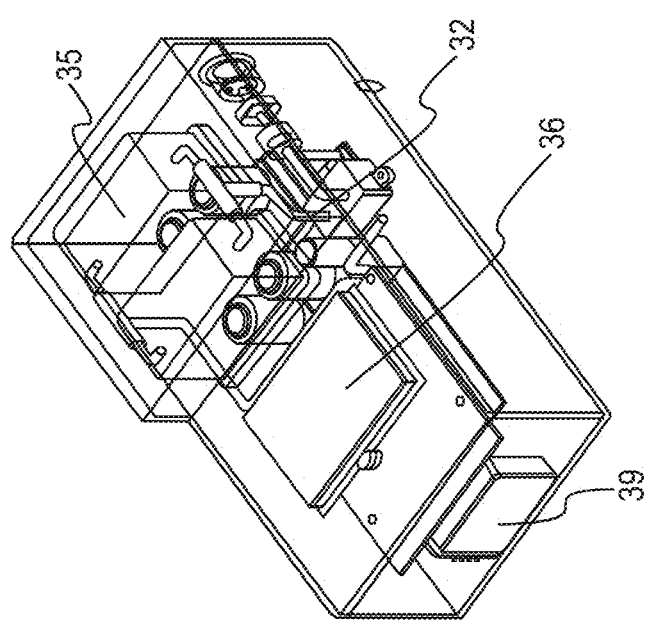

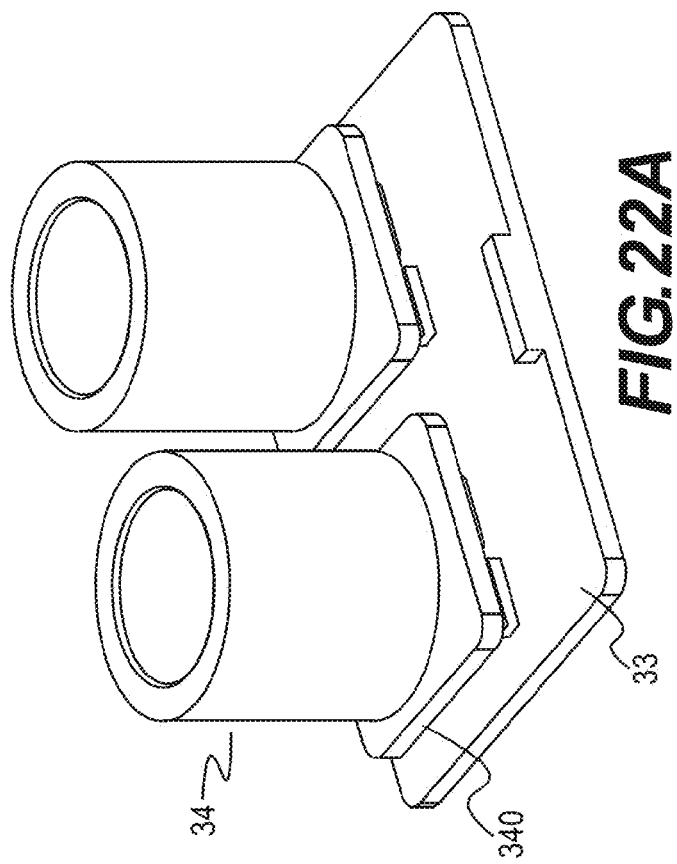
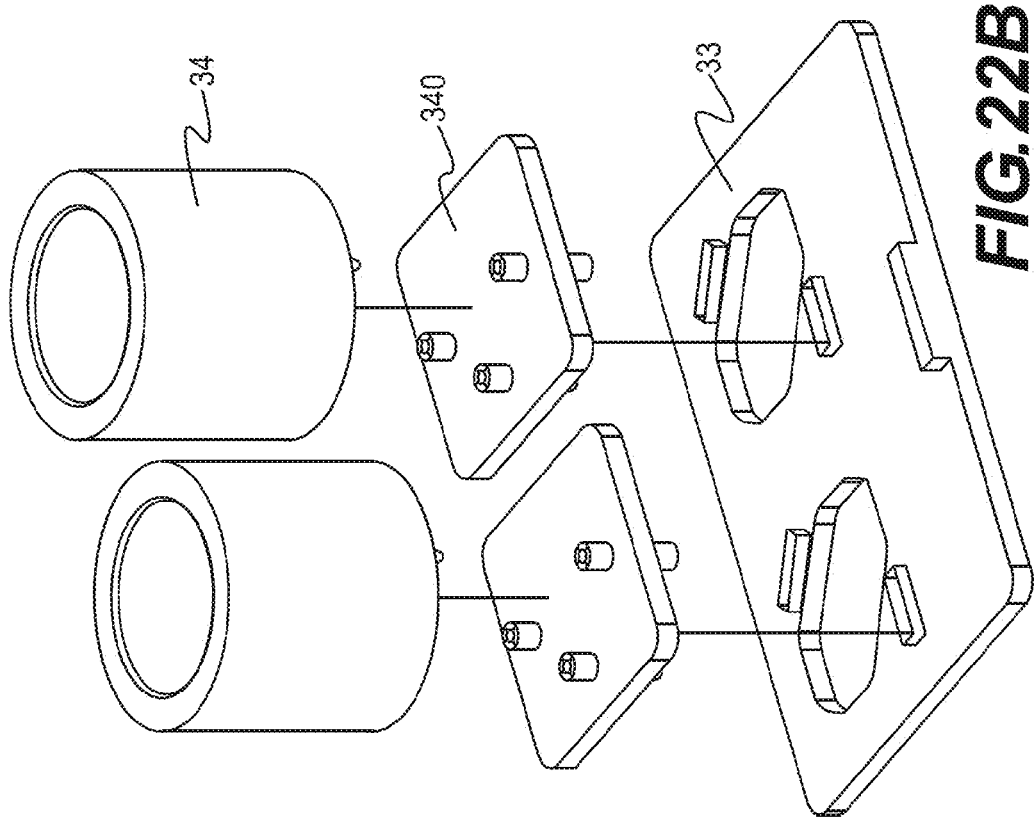

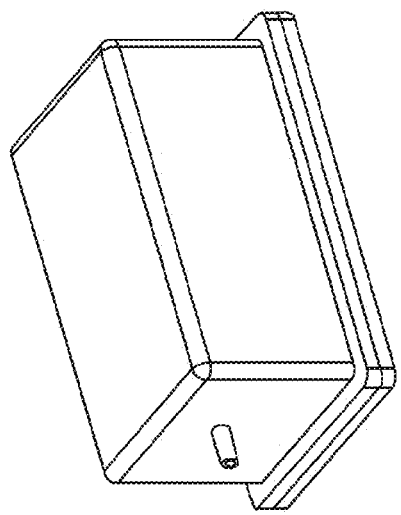
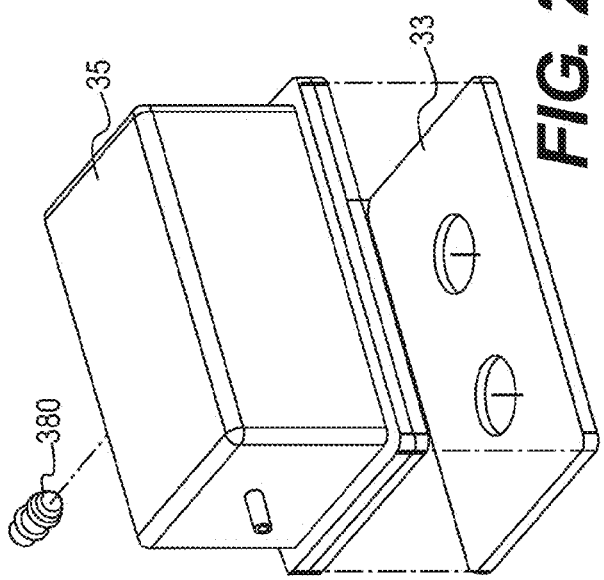
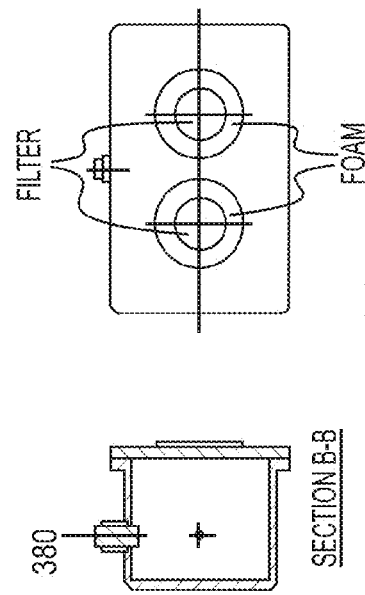
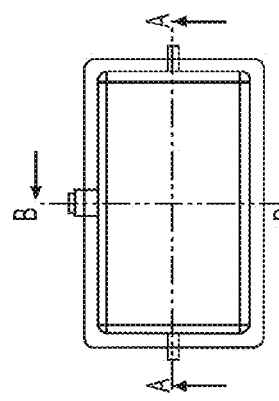

RESULTS OF PUGH ANALYSIS

| GAS | FORMULA | TYPICAL RANGES | SUGGESTED TECHNOLOGY | ALTERNATE TECHNOLOGY |
|---|---|---|---|---|
| HYDROCRABONS - METHANE | CH4 | 0-10,000 ppm | SEMICONDUCTOR | INFRARED |
| CARBON DIOXIDE | CO2 | 0-10,000 ppm (0-1 %vol) | INFRARED | SEMICONDUCTOR |
| HYDROGEN | H2 | 0-1,000 ppm, 0-10,000 ppm, 0-100% LEL | ELECTROCHEMICAL | SEMICONDUCTOR |

*FIG. 24*

METHODS AND DEVICES FOR DETECTING BOWEL PERFORATION

CROSS-REFERENCE TO RELATED APPLICATION

This application claims priority to U.S. Provisional Application Patent Ser. No. 61/473,592 filed Apr. 8, 2011, the entire contents of which are incorporated herein by reference.

FIELD OF THE DISCLOSURE

The present disclosure relates to methods and devices to detect perforation of the bowel, for example, resulting from surgical procedures, such as laparoscopy; diagnostic procedures, such as colonoscopy; medical conditions, such as diverticulitis; and trauma. The present disclosure also relates to filtration systems and electrical connector assemblies for use in the methods and devices.

BACKGROUND OF THE DISCLOSURE

Bowel perforation injuries can occur as the result of surgical procedures; diagnostic procedures; medical conditions; and trauma. The cost to repair a bowel perforation suffered during laparoscopic surgery is minimal if that perforation is identified and treated during that surgery. The cost of reparation, as well as patient morbidity and mortality are far greater if a bowel perforation is not detected at the time of surgery. Cost and morbidity increase as time to diagnosis/intervention increases. Patients suffering undetected bowel perforations during laparoscopic surgery require additional surgery to treat the perforation. Additional diagnostic procedures, hospitalization and surgical intervention such as, CT scan, exploratory laparotomy or laparoscopy, colostomy, ileostomy, reanastomosis, antibiotic treatment, hospitalization/ICU treatment, and infectious disease consultation may also be required. The negative effects from a delay in treating bowel perforations can range from mild peritonitis to septic shock. Sepsis and septic shock can lead to hypoxia, renal failure, other major organ dysfunction and death.

Laparoscopic surgeries are performed to treat a variety of conditions in the abdominal and pelvic area, including but not limited to, exploratory biopsies, cholecystectomy, hysterectomy, hernia repair, ovarian cyst removal, and prostatectomy. Additionally, laparoscopic surgeries are being performed more routinely on patients who might previously have received open laparotomies, for example, in patients who have had previous abdominal surgeries with known adhesions, and for more complex surgeries, such as those involving large tumors, reconstructive surgeries, complex partial nephrectomies, surgeries to treat inflammatory pathological conditions, and all robotic assisted procedures.

Robotic-assisted laparoscopic procedures are also being used with increased frequency in gynecological, urological and other laparoscopic surgical procedures. This further increases the number and complexity of laparoscopic surgeries that are routinely performed. Lack of surgeon feel, as well as reduced visualization associated with robotic assisted laparoscopic procedures can contribute to the risk of bowel perforation and decrease the possibility of immediate detection.

Bowel perforation injuries are a risk associated with laparoscopic surgery. They can occur during initiation of the procedure as a Veress needle or trocar is introduced blindly into the abdominal cavity or during intraoperative dissection and cauterization. Bowel perforation injuries are not easily visualized by medical personnel during surgery due to optical limitations of the surgical equipment. Since the bowel moves during surgery, an area of injury can become positioned outside of the field of vision of the surgeon. Because of the difficulty in visualizing bowel perforations at the time of injury, there is an increased chance that the injury will not be detected during the procedure leading to the above-described negative health effects and increased costs of treatment.

In addition to surgical bowel perforations, patients may suffer trauma or ruptured diverticula causing bowel perforations that are difficult to diagnose by CT scan and clinical examination. Diagnosis relies on CT scans which can result in false negatives and clinical findings often present 24-28 hours after the onset of the infectious process. Bowel perforation is a surgical emergency. Time to diagnosis and treatment are directly correlated with morbidity/mortality and patient outcome.

There remains a need in the art to be able to detect bowel perforation. Optimally, such detection should occur near the time of injury, for example, during a laparoscopic procedure. This need and others are met by the present invention.

SUMMARY OF THE DISCLOSURE

The present disclosure relates to methods and devices for detecting bowel perforation injuries. Such methods and devices involve detecting in an abdominal or pelvic cavity an elevated concentration, as compared to the ambient concentration or a previously recorded concentration, of at least one gas normally found in the bowel. As described herein, a bowel perforation detection device, also referred to as a bowel perforation detection system, can include: a sample delivery unit comprising an aspirate filtering means; a sensing unit comprising a gas-detecting means, a pump, a processor, and a display; and a connector, for example, an electromechanical connector, to link the sample delivery unit and the sensing unit.

The aspirate filtering means can comprise a first filter for separating liquid from aspirate and a second filter for separating gas and microbes from aspirate. The first filter can be a hydrophobic porous membrane filter having pore sizes ranging from about 100 microns to about 500 microns. The second filter can be a hydrophobic filter having a minimum pore size of 0.2 microns or a hydrophilic filter having a minimum pore size of 0.01 microns. The aspirate filtering means can also be a filtration system which includes an outer housing section; an inner tubing section, a portion of which is perforated; a sleeve comprising an absorbent wicking material positioned between the perforated tubing and the outer housing; and the above-described filters. The absorbent wicking material can be a hydrophilic polyurethane foam or a cellulose fibrous material with capillary wicking characteristics.

The gas-detecting means can be one or more gas sensors. User-interactive software can be provided for control of the gas sensors. Any sensors known to those skilled in the art that are capable of detecting the desired gases may be used in the practice of the invention. For example, the gas sensors can be contact gas sensors, non-contact gas sensors, and combinations thereof. Gases that can be detected include, but are not limited to, hydrogen, methane, carbon dioxide, sulfide, and nitrogen. Thus, devices of the invention may include one or more of a carbon dioxide gas sensor, a methane gas sensor, a hydrogen gas sensor, a sulfide gas sensor, and/or a nitrogen gas sensor. The carbon dioxide and methane gas sensors can be infrared sensors and the hydrogen gas sensor can be a solid state sensor. The gas-detecting means can be configured to detect the concentration of gases in real-time.

As described herein, a method for detecting a bowel perforation injury can include steps of: obtaining an aspirate sample from an abdominal or pelvic cavity of a patient; filtering said aspirate sample to separate a gas component of the sample from a liquid component (if present) and a microbial component (if present); analyzing said gas component using a gas-detecting means to determine the composition of the gas contained in the abdominal or pelvic cavity; wherein an elevated level of a gas normally present in the bowel and not normally present in the abdominal or pelvic cavity indicates the presence of a bowel perforation injury. The method for detecting a bowel perforation injury can be accomplished using the devices described herein.

Also described herein is an electromechanical connector. The connector can be used to connect the sample delivery unit and the sensing unit of the bowel perforation detection device. The connector can comprise a first section comprising an insert molded curvilinear conducting element; and a second section comprising a paired pin conductor set. The connector can be an injection molded threaded coupler with a simple standard luer connection containing a metallic conducting strip that is insert molded with the main connector body. This metallic conducting strip will preferentially mate with its counterpart on the sensing unit only when the luer connector is properly threaded on to the sensing unit.

DESCRIPTION OF THE DRAWINGS

FIG. 1B shows another configuration of the bowel perforation detection system.

FIG. 9 is an exploded view of a filter-tubing system as disclosed herein.

FIG. 11 is an exploded view and cross-sectional view of another filter assembly/filtration unit as disclosed herein.

FIG. 12 is an exploded view and cross-sectional view of another filter assembly/filtration unit as disclosed herein.

FIG. 13 is an exploded view and a cross-sectional view of another filter assembly/filtration unit as disclosed herein.

FIG. 15 is a schematic view of an electrical connector disclosed herein.

FIG. 18 is an exploded view and perspective view of a sensor arrangement as disclosed herein.

FIG. 20 is a perspective view of another sensing module disclosed herein.

FIG. 22 is an exploded view and perspective view of another sensor arrangement as disclosed herein.

FIG. 23 is an exploded view, perspective view, and cross-sectional view of another sensing chamber assembly as disclosed herein.

FIG. 24 is a table of sensor selection results.

DETAILED DESCRIPTION

The methods and devices disclosed herein can detect the presence and/or measure the concentration gases that are present in the bowel but not normally present in the abdominal or pelvic cavities. By detecting and measuring these gases, the methods and devices can be used to diagnose the presence and location of a bowel perforation.

Figure 32:
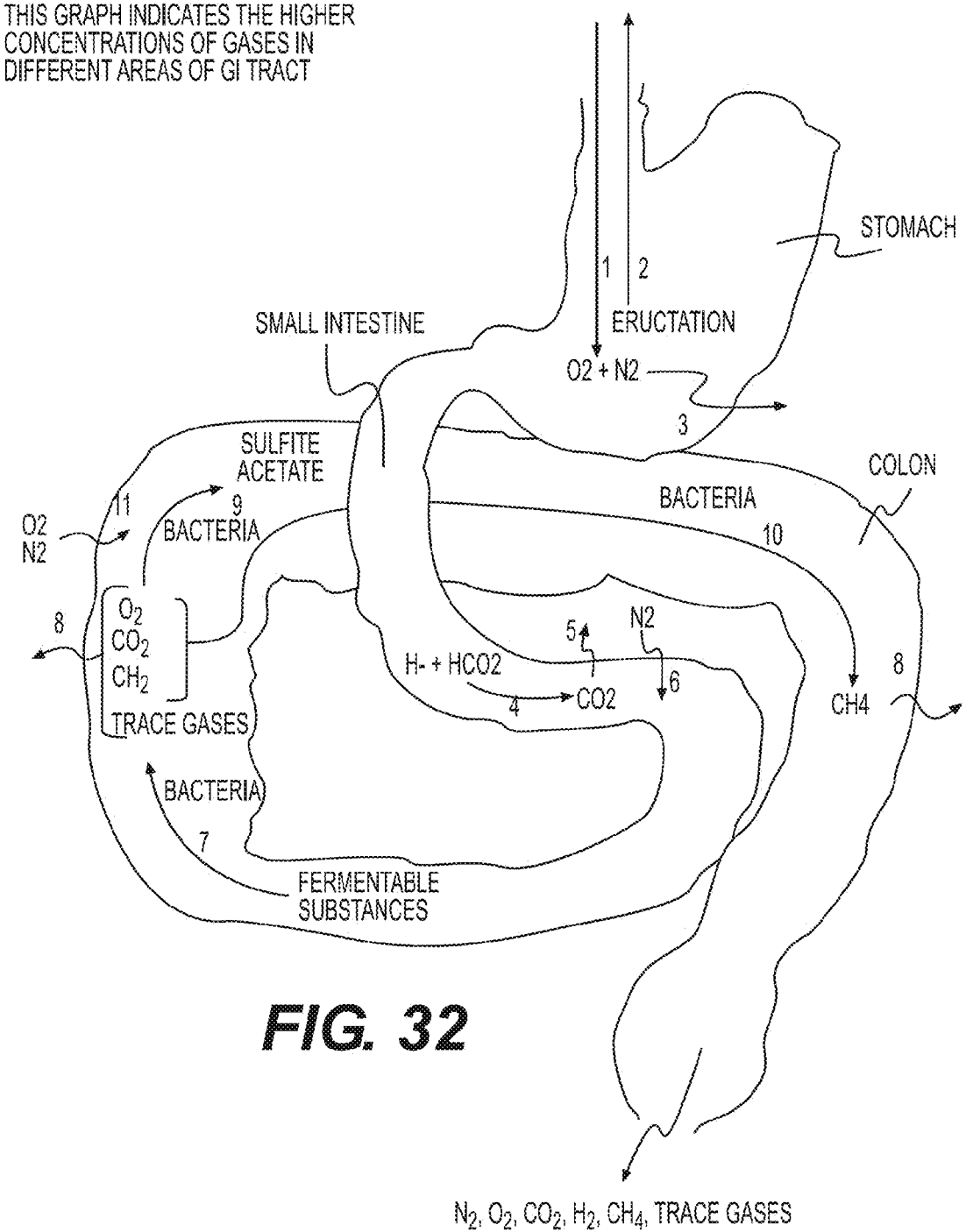
FIG. 32 is a view showing various gas concentrations over the length of the human intestinal tract.

The device disclosed herein can access the abdominal or pelvic cavity, for example, by having a medical device that is positioned in the cavity connected thereto, such as a Verress needle or trocar connected to the device via a Luer Lock. The gas detection device can gently suction a small sample of the air from the abdomen. The device measures for one or more of methane, hydrogen, carbon dioxide, sulfide, and other fermentable gases that are released by bacterial metabolism, such as nitrogen and sulfide acetate. These gases form and are exclusive to the bowel and are not present in the abdominal cavity. These gases exist in different concentrations in each section of the small and large bowel, as shown in FIG. 32. When these bowel gases are discovered in the abdominal cavity, it alerts the physician that a bowel leak or a perforation can exist. The device can also be calibrated based on ambient concentrations of gases for comparison purposes, for example, in order to identify whether an elevated gas concentration in the abdominal cavity could be the result of trace amounts of the gas in the ambient atmosphere of an operating room. The device can also be utilized to detect changes in gas concentrations in the abdominal cavity over time, for example, throughout the course of a laparoscopic surgical procedure.

The device can also analyze the concentration of the different gas types that are present in the abdominal cavity, for example, in order to identify the presence of an abnormally high concentration of a gas and the most likely area of the bowel where that concentration of gases normally resides and escaped into the abdominal cavity. The device can include a processor that identifies the most likely section of the bowel that has been perforated based upon the relative concentrations of bowel gasses, or may be provided with a reference chart so that the physician can direct attention to the most likely area of injury.

The bowel perforation detection device disclosed herein can include a sample delivery unit and a sensing unit. The sample delivery unit and sensing unit can be linked via a connector, for example, an electromechanical connector.

The sample delivery unit can include a means for filtering, for example, a means for filtering aspirate contained in the abdominal and pelvic cavities. The abdominal cavity is a dry space and the sampled aspirate is typically composed mainly of gas. However, the aspirate can contain residual quantities of liquid and can also contain microbes. The filtering means is provided in order to separate any liquid and microbial components of the aspirate from the gas components of the aspirate prior to analysis by the gas sensing means. Separation of liquid components of aspirate is necessary in order to prevent damage to or interference with the gas detecting means, especially when the gas detecting means is a gas sensor. Separation of microbial components of the aspirate is needed in order to contain microbes in the sample delivery unit to prevent contamination of the sensing unit and gas detecting means. By preventing contamination of the sensing unit and gas detecting means, these parts of the device can be reused with other patients and in other procedures.

The filtering means can be a filtration system comprising at least one filter, for example one, two, three, or more filters. The filters of the filtration system can be a coarse hydrophobic filter for fluid separation, i.e., filtering any liquid component present in the aspirate, and a fine filter, for example, a gas filter, to remove particles and other contaminants, for example, microbes, from the aspirate. The sample delivery unit can be pre-sterilized and positioned in the sterile area during a surgical procedure. The sample delivery unit can be disposable.

The sensing unit can include a gas-detecting means. The sensing unit can be positioned in the non-sterile area of the operating room and can be reused.

The gas-detecting means can be, for example, at least one gas sensor. Depending on the type of gas to be detected, the gas-detecting means can comprise more than one sensor, for example, a separate gas sensor for detecting each of carbon dioxide, methane, hydrogen, sulfide, and/or nitrogen. The sensor(s) can be configured to detect these gases sequentially or simultaneously. The sensor(s) can be positioned on a sensor board which may be housed in a chamber. The gas-detecting means can be positioned in the sample delivery unit and results of the gas detection can be transmitted to a separate display unit via a connected or wireless communications interface. The unit can also be provided with an audible alarm that is programmable to indicate when a particular gas concentration exceeds a threshold concentration.

The sensing unit can also include elements related the transport of a gas sample through the unit, for example, tubing for transporting the gas sample from the connector to the gas-detecting means and clearing a tested sample, an exhaust or vent system for discarding the gas sample, and a pump for drawing the aspirate sample through the sample delivery unit and the sensing unit. The sensing unit can also include a processor and display unit for outputting the gas-detecting results.

The connector between the sample delivery unit and the sensing unit can be an electromechanical connector. The electromechanical connector can include an electrical switch to indicate connection between the sample delivery unit and the sensing unit. In some configurations, the connector can be positioned so that a first portion of the connector, for example, a male portion, is positioned as part of the sample delivery unit and a second portion of the connector, for example, a female portion, is positioned as part of the sensing unit. Alternatively, the connector can be positioned completely within the sample delivery unit.

The detection system described herein can make use of several features designed to aid ease of use. For example, the design of the sensing unit, coupling mechanisms, and location of the sensing unit within an operating room can be configured for ease of use by an operator. For example, the device can be located on a battery charging dock on the wall of the operating room in an appropriate location and docked when ready to use and connected to a tubing connector as part of hand-off from within sterile field. An alternate device location is a hand held unit prepped on non-sterile tray with sterile connector tubing etc sealed in its packaging. The device can also be positioned on an insufflation delivery and monitoring stack.

User interface simplicity can be achieved in the design by providing the user a simple button system that allows for a usage sequence in a minimal number of steps, for example, two or three steps. A three-button system can provide an easy method for using the device, for example, as follows: Button A—On/Off Button B—Calibrate (meaning calibrate baseline gas levels in ambient air to measure sample against) and Button C—Start/Stop (meaning turn the pump on to draw in the gas sample for measurement. The software algorithms controlling the pump in the sensing unit can stop the pump automatically once it has drawn enough sample gas in and can also be configured to contain a manual stop option.

The devices disclosed herein can also be designed to have reusable sections, for example, a reusable sensing unit or display unit for use across patients and procedures. Since the device involves transport of gaseous and liquid contents through the tubing, this becomes an especially challenging problem which has been addressed in this system.

Management of the intra-device sterile boundary (i.e., the flow path) is critical and can been accomplished by incorporating a two-stage filtration system, also referred to as a filter system, as the filtering means into the sample delivery unit. The filtration system can be integrated into tubing that connects the device at its distal end to a Veress needle or trocar inserted into the abdominal or pelvic cavity of a patient. The two-stage filtering unit can contain a microbial filter and a gas filter system in conjunction with a liquid bypass absorption element that reliably prevents the ingress of intra-abdominal contaminants (e.g., liquids, and bacteria) from contacting the gas-detecting means, e.g., the gas-sensors. This filtration system can greatly reduce or eliminate the possibility of contaminating the sensors and sensing unit. A third stage gas filter can also be incorporated into the sensor for use during a calibration cycle, i.e., a cycle of the device to detect the ambient carbon dioxide content in an insufflated patient.

The device can be designed to accommodate aspirate volumes as needed to enable detection, for example, from about 50 cc of aspirate to about 500 cc. Since the aspirate can contain residual amounts of liquid in addition to gas (e.g., bowel gas if perforation has occurred, and atmospheric gases resulting from hiss test ingress of outside air), the system can be designed to eliminate liquid ingress via a two-stage liquid bypass filter and in conjunction with a software algorithm controlling the pump such that the liquid breakthrough pressure of the filters is not exceeded by the pump. Thus, the device can achieve filtration of aspirate to separate the liquid and gas phase, and retain enough pressure differential to achieve transport of gas phase to the sensing unit without exceeding the liquid breakthrough pressure of the filter itself.

Figure 4:
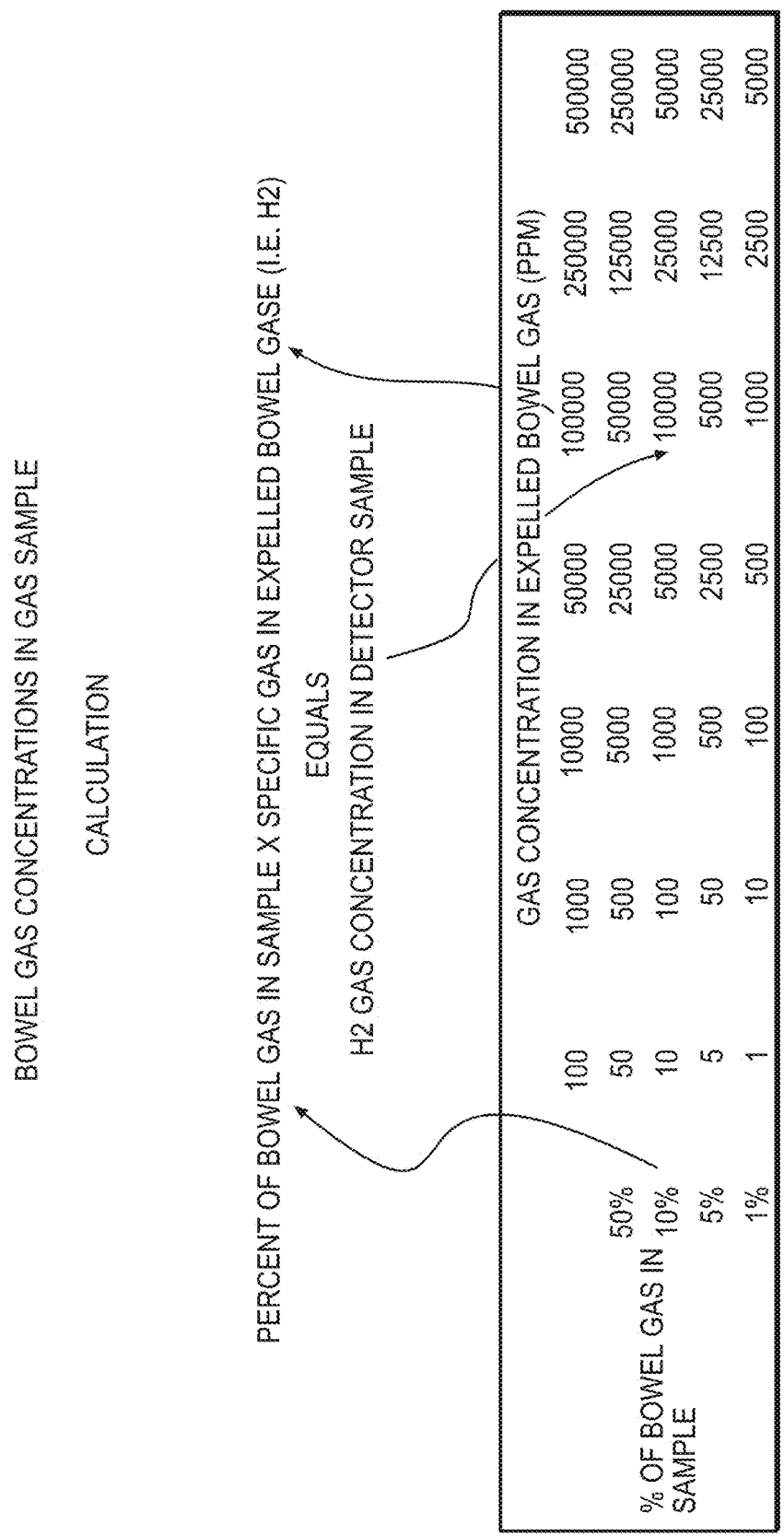
FIG. 4 is a table of calculations for determining bowel gas concentrations in a gas sample.

The system can be designed to accurately detect minute quantities of bowel gases in a sample that are above the threshold levels (ambient concentrations). Bowel gas concentrations are 50,000-290,000 PPM for $CO_2$, 600-470,000 PPM for $H_2$, and 0-260,000 PPM for $CH_4$. Ambient values for each of these gases are 360 PPM, 0.5 PPM, and 2 PPM respectively. The gas-detecting means for each of the gas species in the present device can detect gas concentration elevations of about 1 PPM above ambient concentrations for $H_2$, 10 PPM for $CH_4$, and 100 PPM for $CO_2$, at the sensing unit. The gas concentrations for various sample volumes are shown in FIG. 4.

The bowel perforation detection device disclosed herein is now described with reference to the figures.

Figure 1A:
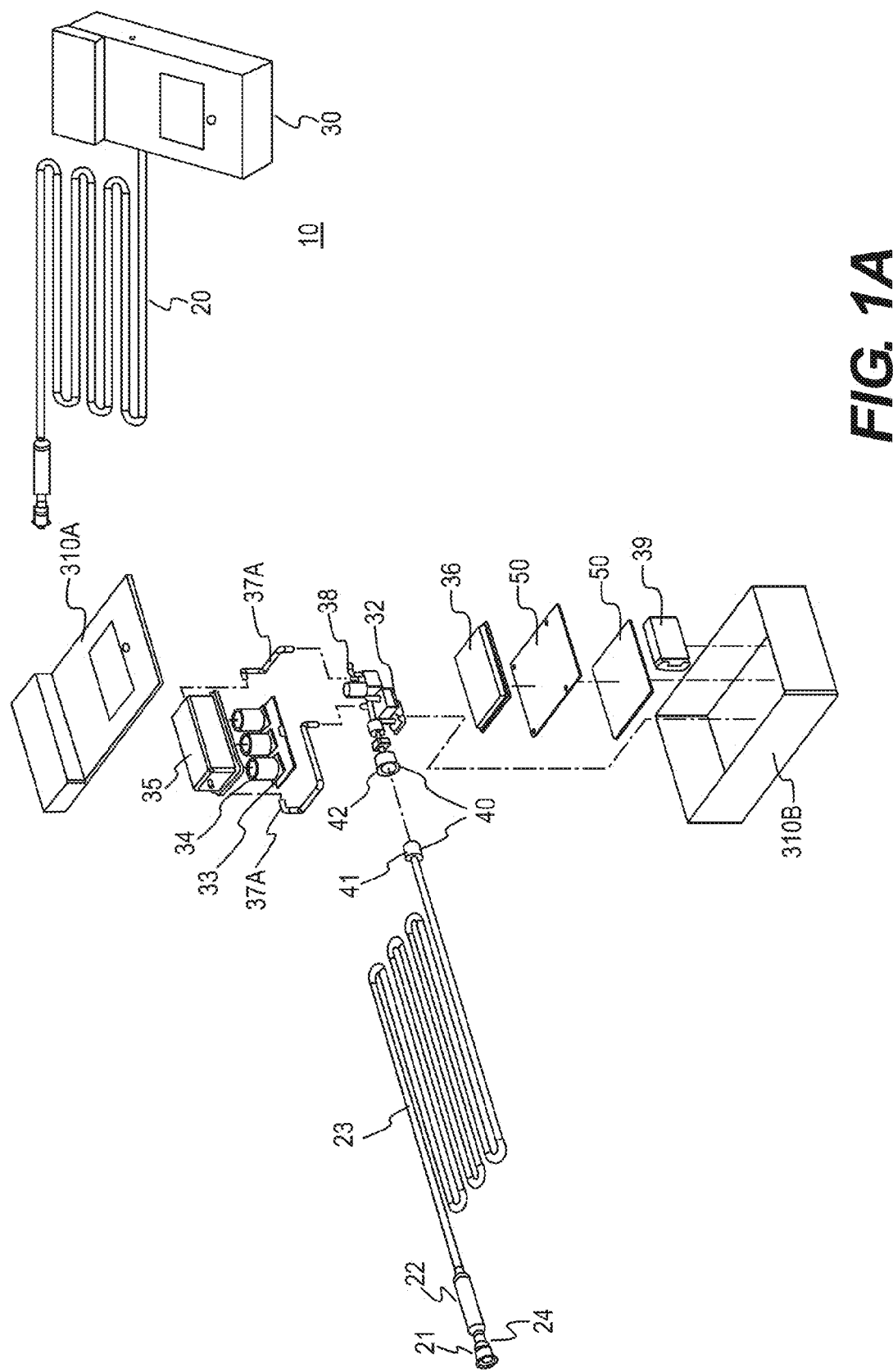
FIG. 1A shows a configuration of the bowel perforation detection system disclosed herein.

FIGS. 1A and 1B provide perspective and exploded views of the device 10. In general, devices of the invention will comprise a sample delivery unit 20 and a sensing unit 30. As shown in FIGS. 1A and 1B, the sample delivery unit 20 can include a luer 21, a means for filtering aspirate that is a filtration unit 22, tubing 23, and a section, for example, a male section 41, of the connector 40. The luer is adapted to be connected to surgical device for accessing the abdominal or pelvic cavities and for obtaining an aspirate sample for passing through the sample delivery unit to the sensing unit 30, for example, a Veress needle or trocar (not shown). The luer can also be provided with a one way valve 24 in order to prevent return of sampled aspirate into the abdominal or pelvic cavity.

As shown in FIGS. 1A and 1B, the sensing unit 30 can include a housing unit, shown as top housing unit 310a and bottom housing unit 310b, a section, for example, a female section 42, of the connector 40, a gas-detecting means, a pump 32, a processor 50, tubes 37a (FIGS. 1A and 1B) and connectors 37b (FIG. 1B) for transporting the sample through the sensing unit, an exhaust/pressure relief system 38 for venting sampled gas, a battery 39, and a display unit 36. As shown in FIGS. 1A and 1B, the gas detecting means can be a sensor board 33 having at least one gas sensor 34 that is housed in a sensing chamber 35. The sensing chamber can have ports for transporting the gas sample into and out of the chamber. The chamber can also have a pressure relief valve. The pump 32 is provided to draw the aspirate sample from the abdominal or pelvic cavity, through the sample delivery unit, and into the sensing unit. The number, position, shape, and length of tubes 37a and connectors 37b in the sensing unit are not particularly limited and can be adjusted as understood by one of ordinary skill in the art to transport the gas sample through the sensing unit 30 and sensing chamber 35.

FIGS. 1A and 1B show alternate configurations for the sensing chamber. As shown in FIG. 1A, the sensing unit has a single sensing chamber. A single sensing chamber configuration is discussed in more detail below with reference to FIGS. 16-19. As shown in FIG. 1B, the sensing unit has two sensing chambers and each chamber can contain different types of gas sensors. A two sensing chamber configuration is discussed in more detail below with reference to FIGS. 20-23. FIGS. 1A and 1B also show alternate positions for the connection of the sample delivery unit and the sensing unit.

The bowel perforation detection system described herein can be configured as a single-stage unit, e.g., a system in which the sample delivery unit and the sensing unit are physically connected. Alternatively, the system can be can be configured as a two-stage unit, e.g., a system in which the sample delivery unit and sensing unit are separate, stand-alone units, or parts of the sample delivery unit and sensing unit are separate. System architectures for single-stage and two-stage units are explained with reference to FIGS. 5-8.

Figure 5:
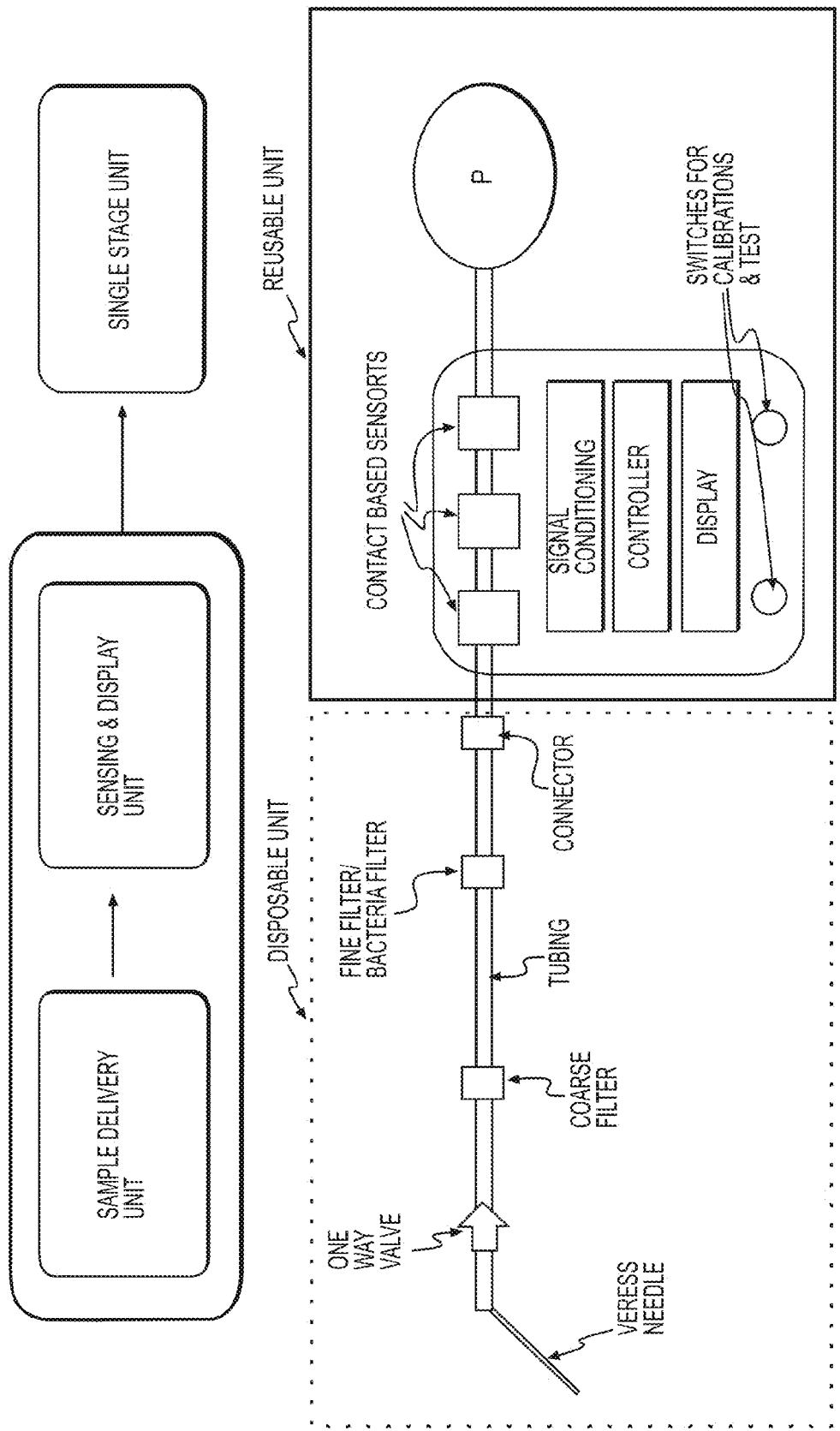
FIG. 5 shows the configuration of a single stage embodiment of the bowel perforation detection system disclosed herein.

FIG. 5 shows a system architecture for a single-stage unit bowel perforation detection system as described herein. A disposable sample delivery includes tubing with a one way valve, at the needle coupling/needle luer, a coarse hydrophobic filter for fluid separation, and a fine gas filter to remove particles, microbes, and other contaminants. The sample delivery unit also contains a coupling to connect to the sensing unit which incorporates an electrical conducting insert that serves as a switch which is triggered if the connector is properly assembled (e.g., threaded) onto the sensing unit. The reusable sensing unit shown in FIG. 5 includes three gas sensors (for example, one for each of $CO_2$, $CH_4$, and $H_2$) in series, a pump, valves, mother board, embedded software, screen display, and switches/user control buttons, as needed, integrated in to a single housing for use. The number of sensors included in the sensing unit can be adjusted based on the number of gases desired for detection. Sensors specified for this application can be contact based requiring direct interaction with the gaseous species (electrochemical and catalytic technologies) to enable concentration measurement. Contact based sensors require more sophisticated software algorithms for driving each sensor (which can be different for each sensor), sensing, and signal conditioning. This system architecture provides for real time intermittent or continuous analysis of the sample and simultaneous detection by the gas sensors.

Figure 6:
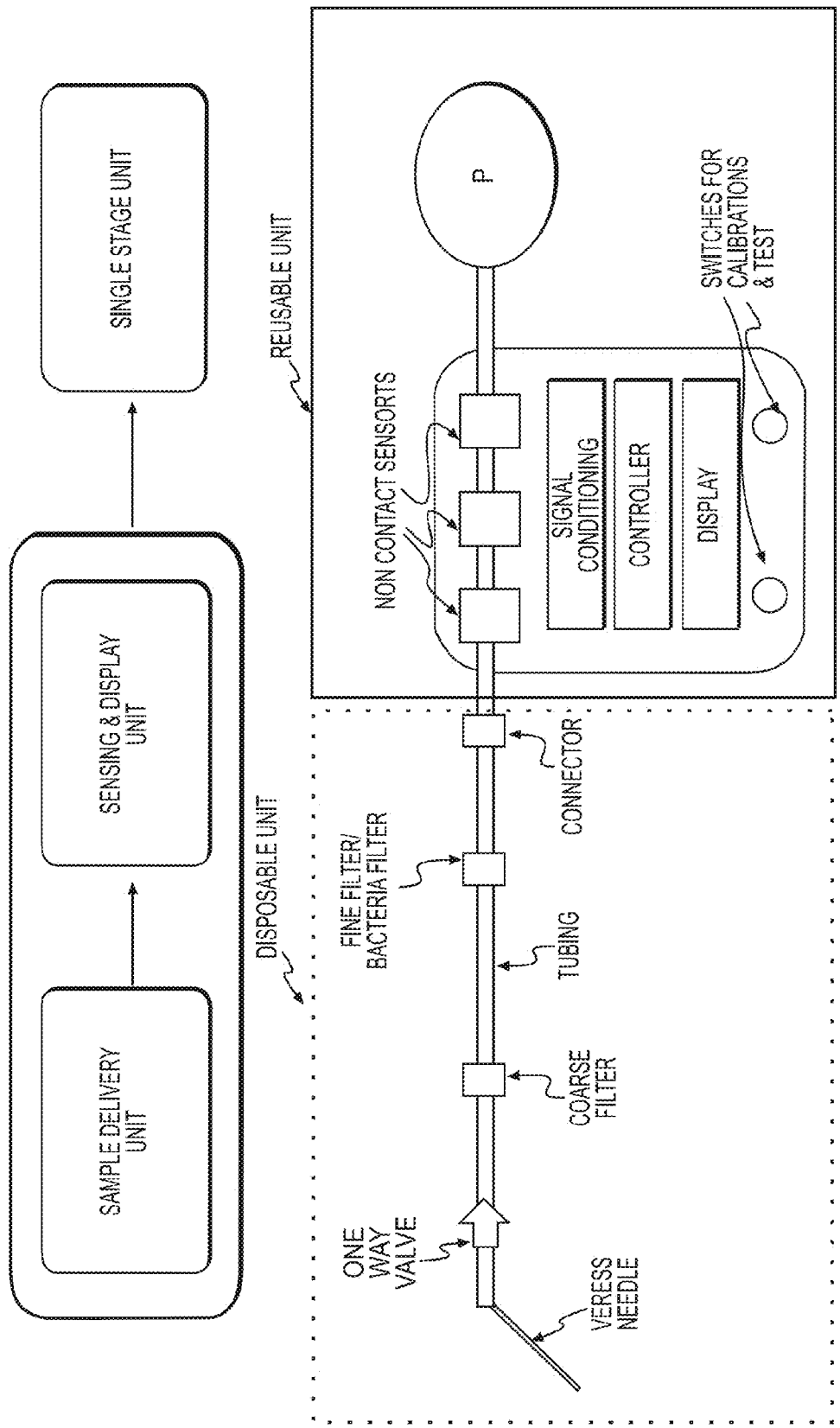
FIG. 6 shows the configuration of another single stage embodiment of the bowel perforation detection system disclosed herein.

FIG. 6 shows an alternative system architecture for a single-stage unit bowel perforation detection system as described herein. The system architecture shown in FIG. 6 is similar to that shown in FIG. 5. The architecture shown in FIG. 6 is designed for utilizing non-contact technologies, such as infrared (optical) methods, for sensing gas concentrations. This system architecture incorporates a similar modular hierarchy with the sample delivery unit containing the valves, filters, tubing, and electromechanical connector, and the sensing unit containing all of the hardware and software used for gas sensing. Non-contact sensors require less sophistication in terms of software algorithms for sensing and signal conditioning. This system architecture also allows for real-time sensing and sequential activation of the gas sample.

Figure 7:
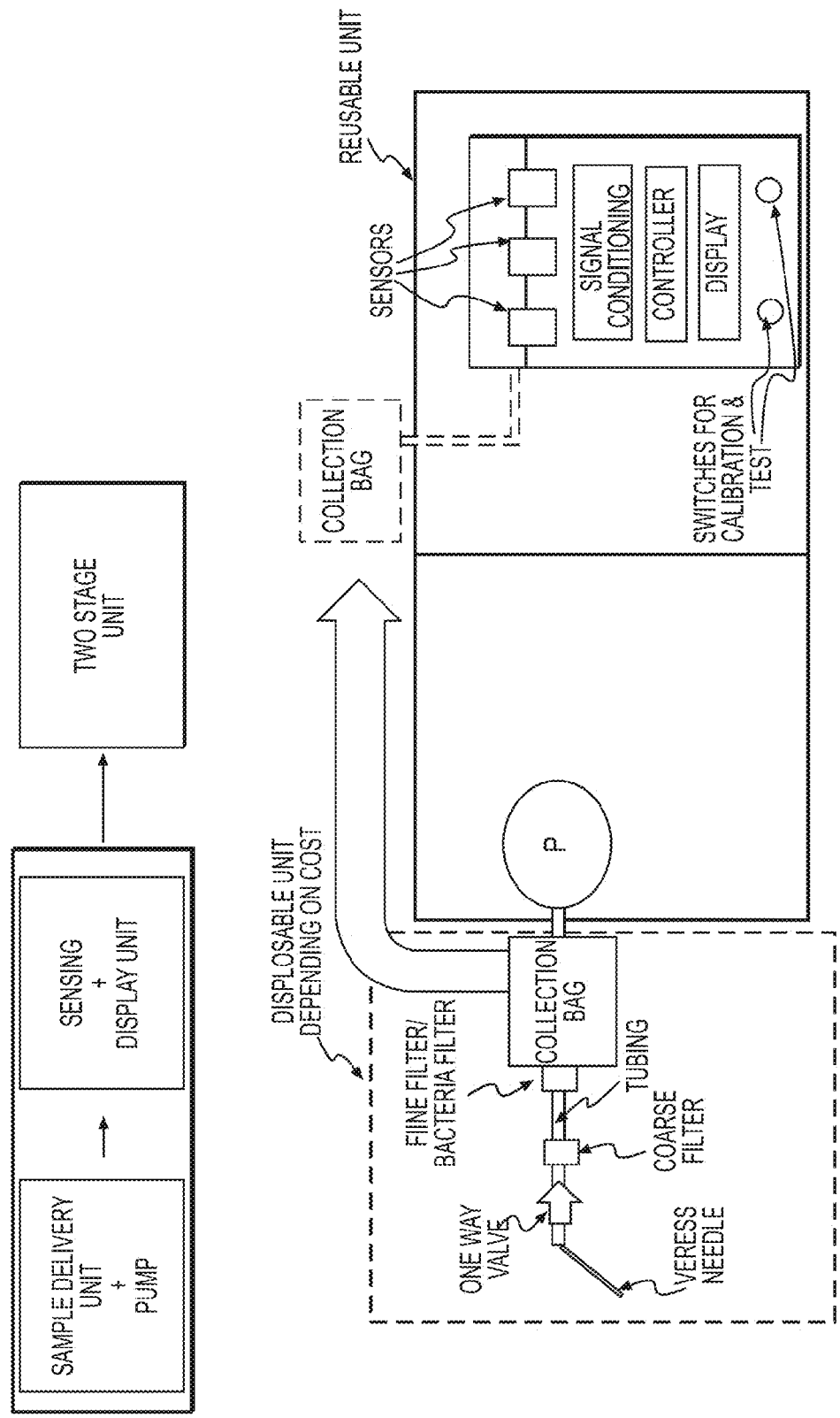
FIG. 7 shows the configuration of a two stage embodiment of the bowel perforation detection system disclosed herein.

FIG. 7 shows a system architecture for a two-stage bowel perforation detection system. A two-stage system can be desired in clinical settings where real time tracking of bowel gas leakage risk is not possible, or not required. In these settings, system architecture shown in FIG. 7 can be used, which makes use of the same general principles and design specifications shown in the system architectures of FIGS. 5 and 6. In the system architecture shown in FIG. 7, the first stage contains the sample delivery unit along with a portable pump to collect the gas into a collection bag for storage. The filtered sample gas will be taken offline for sensing and display of the results. For example, the sample is delivered from the sample delivery unit to a collection bag and the collection bag is then disconnected from the sample delivery unit and attached to the sensing unit for transfer of the sample to the sensing unit. The time required to acquire and test a sample with this system is greater than a single-stage unit. This architecture may be useful, for example, in settings where real-time results are not required or desired. This can decrease the cost of the system for both the sample delivery unit and the gas-detecting means in the sensing unit.

Figure 8:
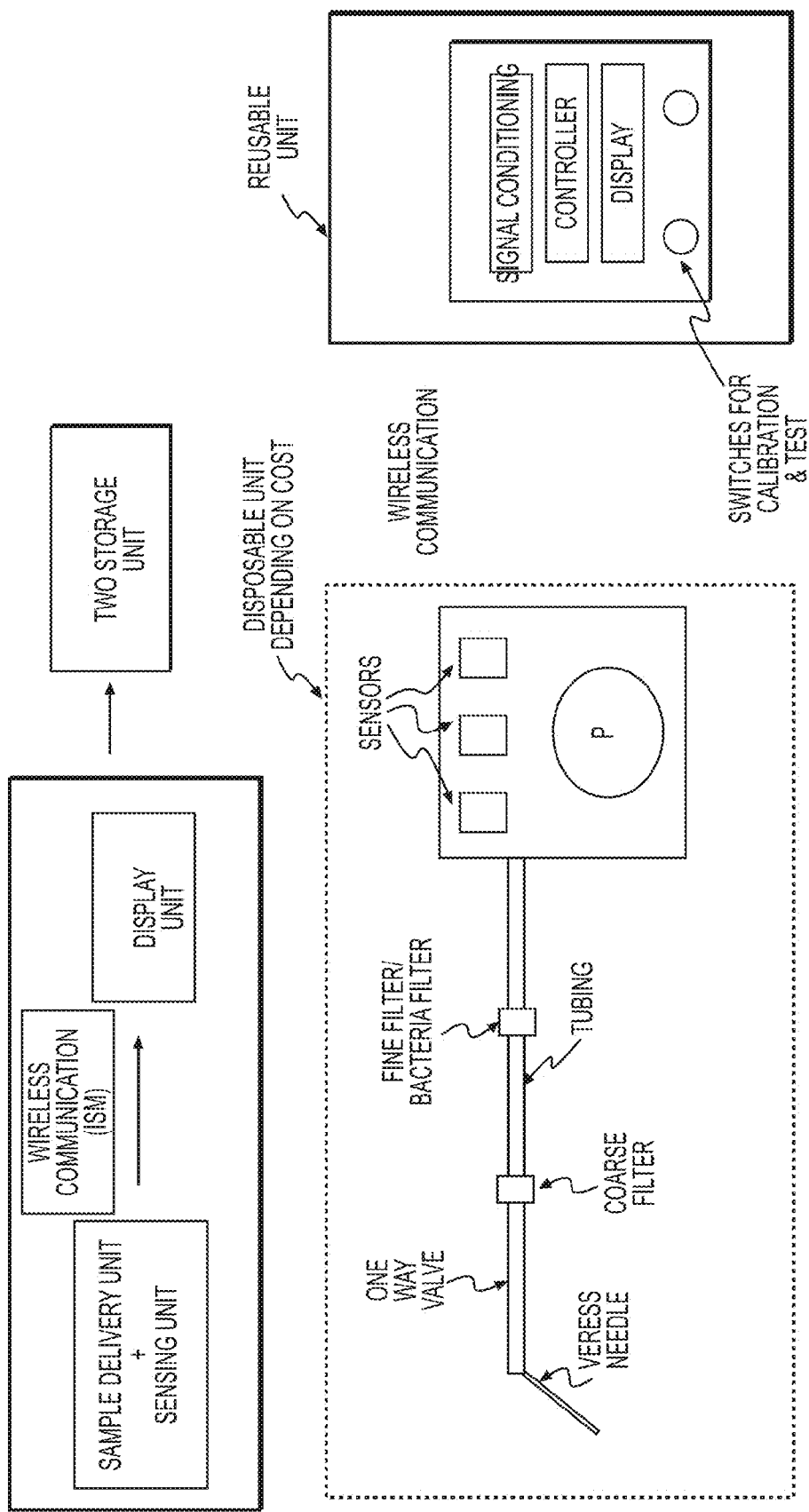
FIG. 8 shows the configuration of another two stage embodiment of the bowel perforation system disclosed herein.

FIG. 8 shows another system architecture for a two-stage unit. This system architecture addresses the issue of having tubing cross a sterile barrier, by eliminating the tubing connection from the sample delivery unit to the sensing unit. In this design, the sample delivery unit includes the gas-detecting means and associated components (e.g., pump, tubing, exhaust) communication between the sampling-sensing unit (disposable) and the display is provided as a separate unit that is connected to the combined sample delivery-sensing unit via a wireless communications interface. Testing results are transmitted via the wireless communications interface for processing and display on the separate display unit.

These above-described system architectures take into account the various requirements including and not limited to various considerations such as sterile barrier, preferential gas transport, shielding of sensing elements from body fluids and other contaminants, pumping requirements, software control algorithms to address ease of use, handling, reliability and accuracy to avoid false positives and false negatives, and disposability of the appropriate modules that do get contaminated. A person of ordinary skill in the art will recognize variations of these system architectures based on these factors.

In addition to features that ensure no fluid ingress into the sensing unit, the filter tubing also incorporates an electro-mechanical connector. The connector can include a mechanical coupling to the sensing unit that also serves as an electrical switch that completes the sensor control circuit when properly connected. This is designed to ensure that the sensing units are not activated without the filter in place, i.e., the unit will not function without filter connected The sample delivery unit can include a filtering means, tubing for transporting the sample through the unit, and a luer adapted for connection to a device for obtaining an aspirate sample, for example, a trocar or Veress needle. The filtering means can be a filtration system comprising at least one filter. The purpose of the filtering means is to separate the liquid, microbial, and gaseous components of aspirate in the abdominal and pelvic cavities. The tubing can be suitable for use in surgical procedures and is not particularly limited by material and size.

The primary function of the filtering means of the present systems are to eliminate any liquid phase components of the aspirate as close to the luer-Veress needle/trocar connection as possible. This can be achieved by using at least one filter as the filtering means. When using a filter as the filtering means, it is also necessary to avoid liquid clogging at the filter, which can trap gas distal to the filter, and to prevent contaminants from entering the sensing unit.

The filtration requirement for transporting bowel gases over a substantial length of tubing has several challenges. These include the need to completely eliminate liquid from entering the gas sensing unit, avoiding clogging of gas filters with liquid and trapping gas near the needle and ensuring that no bacterial contaminants enter the sensing unit. Preventing the entry of bacterial contaminants into the sensing unit is necessary in order to ensure reusability of the sensing unit.

Filter performance characteristics are measured by various types of parameters. Water Breakthrough or Water Entry Pressure (WEP) is a measurement of the pressure required to push water through a hydrophobic filter and is a measure of filter integrity. The bubble point of a filter measures the pressure required to remove liquid from the largest pore of the filter. Flow rate measures the flow of liquid or air through the filter at a given pressure. Housing Integrity is the pressure that the filter housing will withstand before it bursts. Filtration efficiency is a measure of the performance of the filter by comparing the "challenge" with the "filtrate". The selection of the appropriate filter for an application is determined by the composition of the media to be filtered, the desired filtrate, the pressure drop, and flow rate requirements.

Additionally, for systems as described herein which must be designed for use within a sterile area, methods of sterilization are also considered. Filter unit materials can be used which allow for both Gamma sterilization and Ethylene Oxide sterilization.

Based on the above-described goals, a two-stage filtration strategy can be selected. The first stage can involve a first filter for liquid filtration, i.e., separation of the liquid phase from the aspirate. The first filter can be a hydrophobic porous membrane filter with pore sizes ranging from 100-500 microns. Such filters are commercially available from manufacturers as Pall Medical®, GVS®, PSI®, Millipore®. The second stage can include a second filter for gas and microbial filtration and can be a hydrophobic or a hydrophilic filter depending on the size of the contaminants. For a hydrophilic filter, the minimum pore size can be 0.01 microns. For a hydrophobic filter, the minimum pore size can be 0.2 microns.

The presence of these two types of filters does not eliminate all potential clogging risk. Since tubing diameters can be very small, there is a potential risk of clogging or entrapment of liquid aspirate at the first filter, resulting in trapping of the gases on the upstream side of the filter. In this situation the only way to continue to transport gas through the tubing lumen is to increase the pump pressure and exceed the liquid breakthrough pressure for the liquid membrane filter, which then poses a risk of liquid reaching the gas sensing unit. An alternate approach can be to employ a sophisticated pump control (e.g., on-off cycling techniques similar to the antilock braking systems in an automobile) algorithms can be developed based on the LBP pressure cutoffs to create a break in the liquid barrier or agitate the trapped liquid just enough to transport gas through.

In order to avoid the above-described problems, the sample delivery unit can be provided with a filter-tubing system containing a one way valve in series with tubing (internal diameters from 2 mm to a high of 12 mm). FIG. 9 shows an exploded view of a sample delivery unit including a luer 21 for connecting to a surgical device (e.g., Veress needle or trocar), a one-way valve 24, a filtration unit 22 having one end adapted to connect to the one way valve and another end adapted to connect to tubing 23, and a male section 41 of the connector for connection to the sensing unit.

A filtration unit 22 as shown in FIG. 10 can include a rigid outer case/housing 220, a perforated section of tubing 223 that transports the aspirate, an absorbent wicking material sleeve 224 between the perforated inner tube and outer casing, a first filter 221, for example, a liquid hydrophobic large pore (100-500 micron) filter, and a second filter 222, for example, a 0.2 micron hydrophobic or hydrophilic gas/microbial filter, downstream from the first filter. The filtration unit has a lumen through which the aspirate sample passes. The filtration unit can also have a spacer 226 positioned between the liquid filter 221 and gas filter 222. The spacer 226 can have recessed portion(s) for positioning of the filter(s). The filtration unit can have a housing cap 227, which can have a recess for positioning of a filter and an end adapted to connect to tubing. As shown in FIG. 10, a portion of the perforated tubing 223 can protrude from housing 220 for connection to the one way valve.

The perforated section of tubing 223 can have a shoulder portion 228. The shoulder portion can be integrally formed with the perforated section and formed of the same material. Alternatively, the shoulder portion can be a separate component positioned at an end of the perforated tubing. The shoulder portion can have a recessed area for positioning a filter.

Figure 10A:
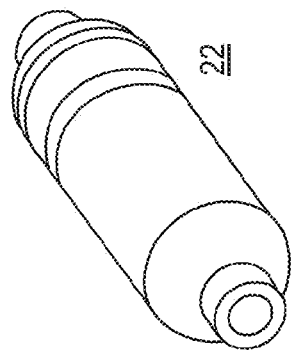
FIG. 10 is an exploded view and cross-sectional view of filter assembly/filtration unit as disclosed herein.
Figure 10B:
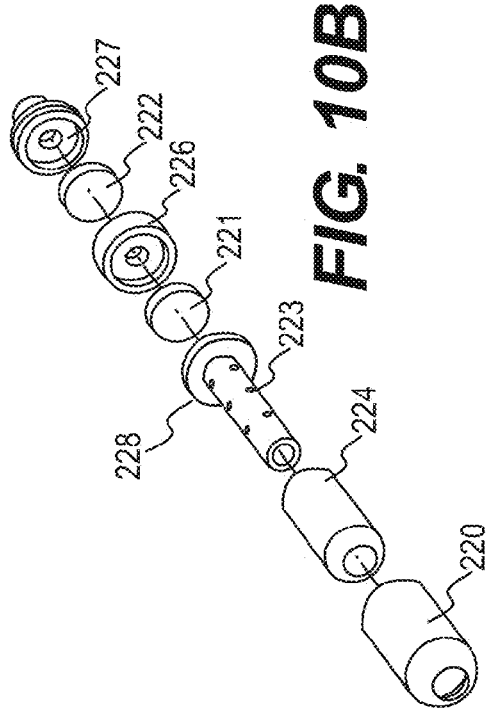
Figure 10C:
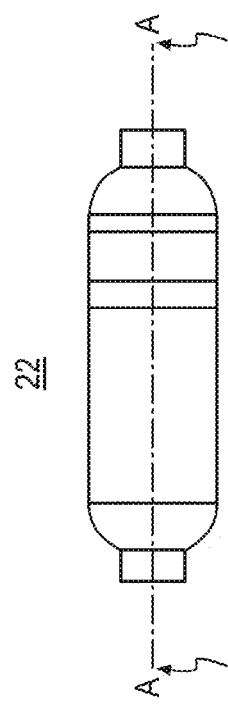
Figure 10D:
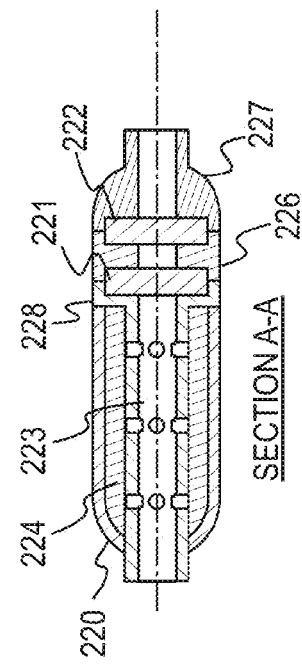

FIGS. 10A and 10B provide perspective and exploded views, respectively, of the filtration unit. FIG. 10C provides another perspective view and FIG. 10D is a cross-sectional view along line A-A of FIG. 10C. FIG. 10D depicts the assembly of a central perforated tubing (shown with multiple perforations around the circumferential and axial direction, the absorbent sleeve, the outer rigid housing that will resist the vacuum pressure applied without buckling in, and the two-stage filter discs for liquid and gas respectively.) As shown in FIG. 10D, an external portion of the filtration unit can be formed by the housing 220, the shoulder portion 228, the spacer 226, and the housing cap 227, which can be hermetically sealed.

This entire assembly comprises a liquid bypass absorption mechanism to prevent liquid entrapment clogging which features the perforated inner tube which allows liquids to be wicked into the absorbent sleeve. Various absorbent materials such as cellulose fiber mats, and hydrophilic urethane foams can be used to achieve the wicking functionality. The wicking functionality allows for liquids to be moved away from the gas flow path and maintain an open lumen for gaseous species transport. The tubing end that couples to the sensing unit has a mechanical connector containing an electrical conductive element that is engaged with a female mating connector on the housing to complete the sensing circuit.

An alternative filter housing design can have only the liquid filter 221 within the filtration assembly (as shown in FIG. 11) and place the gas filter at the coupling site with the sensing device (not shown). This configuration can allow for lower driving pressures at the pump by eliminating or reducing the pressure differential resulting from the length of tubing (approximately 2-3 meters) used for transport of gas species. This feature can enable the selection of smaller and lower pressure capacity pumps for the sensing unit. FIGS. 11A and 11B provide perspective and exploded views, respectively, of the filtration system. FIG. 11C provides another perspective view and FIG. 11D is a cross-sectional view along line A-A of FIG. 11C.

The filtration unit 22 shown in FIG. 11 can include a rigid outer case/housing 220, a perforated section of tubing 223 that transports the aspirate, an absorbent wicking material sleeve 224 between the perforated inner tube and outer casing, and a filter 221, for example, a liquid hydrophobic large pore (100-500 micron) filter. The filtration unit has a lumen through which the aspirate sample passes. The filtration unit can have a housing cap 227, which can have a recess for positioning of a filter and an end adapted to connect to tubing. A portion of the perforated tubing 223 can protrude from housing 220 for connection to the one way valve.

The perforated section of tubing 223 can have a shoulder portion 228. The shoulder portion can be integrally formed with the perforated section and formed of the same material. Alternatively, the shoulder portion can be a separate component positioned at an end of the perforated tubing. The shoulder portion can have a recessed area for positioning a filter.

As shown in FIG. 11D, an external portion of the filtration unit can be formed by the housing 220, the shoulder portion 228, and the housing cap 227, which can be hermetically sealed.

Another configuration for the disposable filter tubing system 22, as shown in FIG. 12, can be provided to address scenarios in which larger quantities of aspirate are desired for testing purposes. In this embodiment, a thin-walled absorbent sleeve 224 and housing 220 can be extended all along the length of the tubing 223 and transport tubing to provide the desired volumetric pore capacity to filter large amounts of aspirate as desired. The filtration unit shown in FIG. 12 includes one filter 221. However, this filter assembly design can also incorporate multiple filters, for example, liquid and gas membrane filters at the end close to the sensing device. The filtration unit can also include a housing unit 220, housing cap 227, and spacer. A portion of the perforated tubing 223 can protrude from housing 220 for connection to the one way valve.

FIGS. 12A and 12B provide perspective and exploded views, respectively, of the filtration system. FIG. 12C provides another perspective view and FIG. 12D is a cross-sectional view along line A-A of FIG. 12C.

Another configuration for the filter assembly 22 is described with reference to FIG. 13. This filter assembly contains an injection molded rigid housing 220 with a first filter 221, for example, a liquid filter membrane (100-500 microns-hydrophobic). This configuration does not contain a liquid bypass feature in place of which, a larger volume chamber 229 within housing 220 is provided with a flared filter surface area to increase flow and prevent liquid entrapment and clogging. Housing caps 227, adapted to connect to tubing, can also be included in the filter assembly. FIGS. 13A and 13B provide perspective and exploded views, respectively, of the filtration system. FIG. 13C provides another perspective view and FIG. 13D is a cross-sectional view along line A-A of FIG. 13C.

Figure 14:
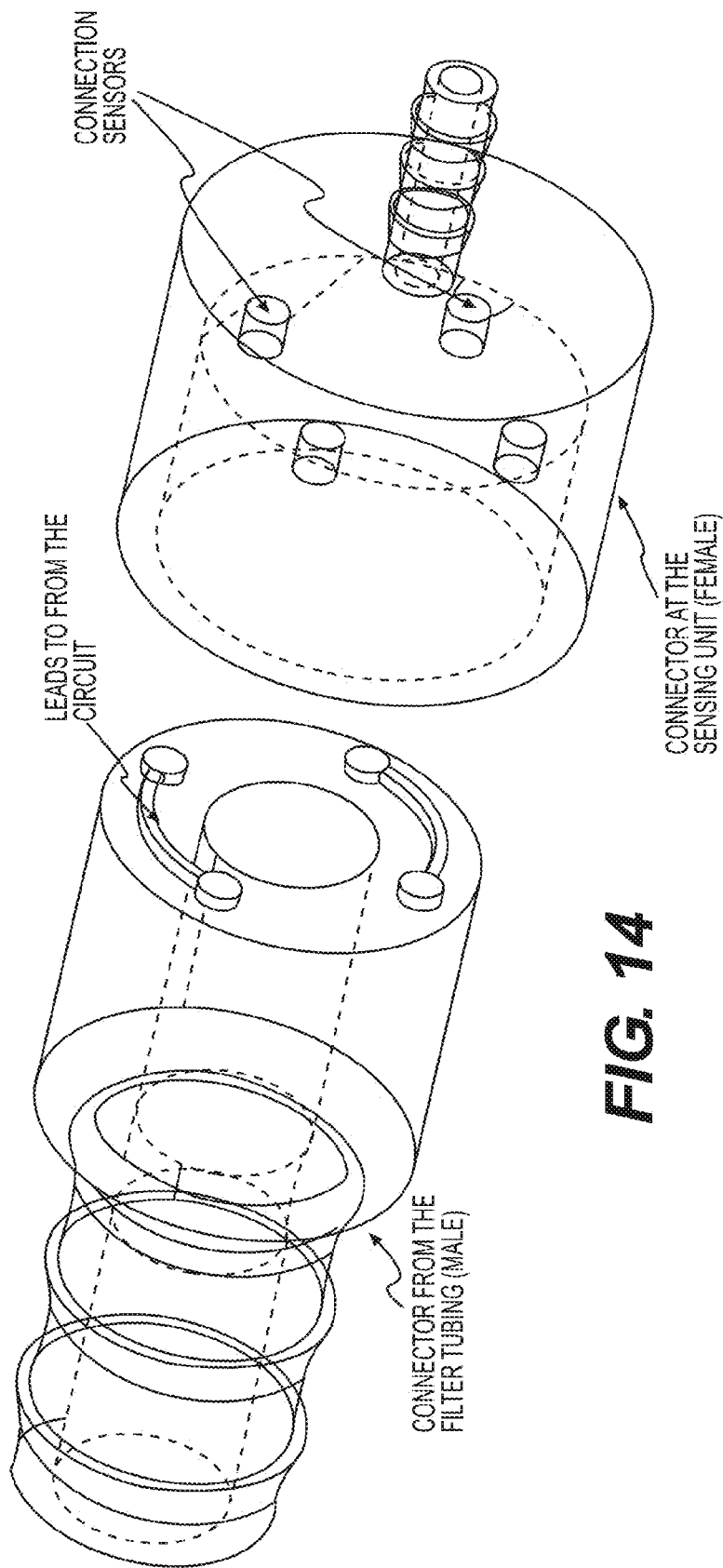
FIG. 14 is an exploded view of an electrical connector disclosed herein.

All the embodiments of the filter-tubing assembly can contain an electrical coupling connector integrally assembled into the tubing. The electrical coupling connector, also referred to as an electromechanical connector, is shown in FIGS. 14 and 15. The mechanical connection can be a bayonet fitment requiring rotation, for example, a 90 degree or a 45 degree rotation, to bring the conductive elements in contact between the tubing connector of the sample delivery unit and its mating counterpart on the sensing unit housing to complete the sensing circuit. The electrical coupling itself can be facilitated by providing electrodes, for example, curvilinear copper or steel electrodes that are insert molded into the plastic connector at the end of the tubing. The curvilinear electrodes can also be stamped from sheet metal and bonded to the plastic connector surface using alternate methods such as adhesive bonding, thermal bonding, and ultrasonic welding. Matching pin electrodes can be located on the female side of the connector located within the sensing unit. The pin electrodes can be in turn connected internally to the circuit that contains the sensors, pumps, mother board, and screen display. This circuit can remain open when the tubing side connector is not assembled to the sensing side connector coupling. When the tubing side connector is threaded on to the sensing side, the rotational lock (e.g., bayonet or standard threaded connection) can bring the electrical conducting strip and pins in alignment, thus completing the circuit. This circuit closure can be detected by a smart software algorithm indicating that the device is ready for use and that the tubing is connected correctly. The loss or presence of this connection will also be monitored by the software algorithm during intermittent or continuous gas sensing modes to ensure that tubing connections are correct and working as desired real time.

The sensing unit can be a hand held device with a housing unit, for example, a rigid plastic injection molded housing, containing an onboard battery pack for power, user interaction screen interface, processor, for example, a processor for signal conditioning, embedded software, pump, flow and pressure sensors, an enclosed sensing chamber with gas sensors, a pressure relief valve as appropriate for venting, and tubing for gas transport. The sensing unit is described in detail with reference to FIGS. 16 to 19.

Figure 16B:
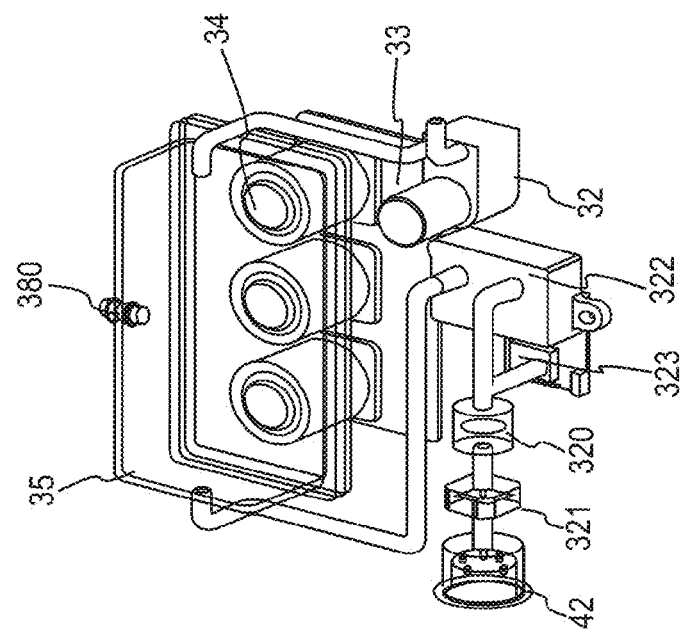
FIG. 16 is a perspective view of a sensing module as disclosed herein.
Figure 16A:
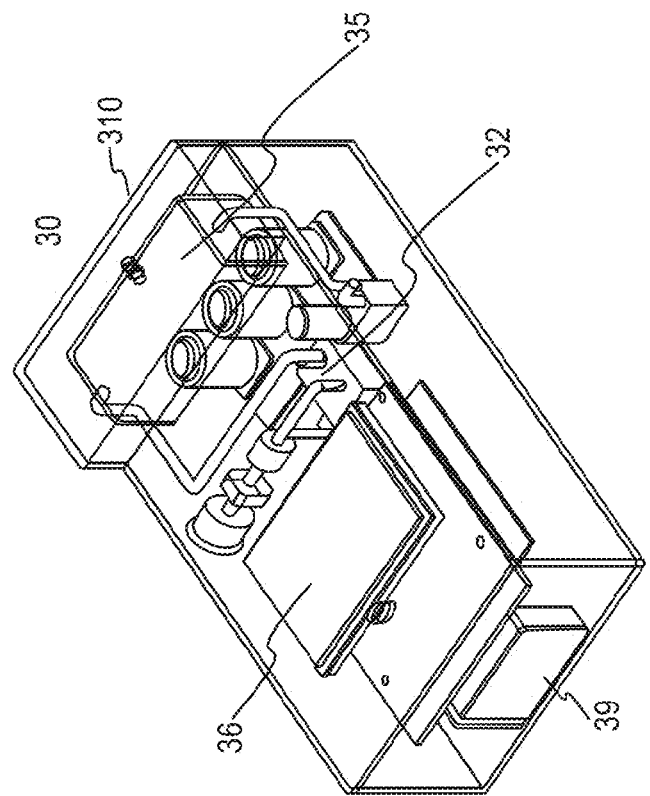

FIGS. 16A and 16B show a sensing unit 30 for use in a single-stage system architecture, for example, as shown in FIGS. 5 and 6. The sensing unit 30 can have a sensing module housing 310 containing a linear array of gas sensors 34 inside a sensing chamber 35. The sensing unit can also include a display 36 and battery 39. Although the system architectures shown in FIGS. 5 and 6 have different modes of gas detecting, the hardware remains the same across both. Although the size of the sensing module housing is not particularly limited, the housing as shown in FIG. 16 is about 210×115×63 mm.

Gas ingress can be achieved when the processor (not shown) starts the pump 32 which opens a one-way valve 320 and enables transport of gas through the internal secondary filter 321. Gas passes through the in-series flow sensor 322 and is transported to the sensing chamber 35 wherein the gas sensors 34, for example, $CO_2$, $CH_4$, and $H_2$ sensors, are sequentially turned on based on the sensor response/reaction times to enable concentration measurement. The sensors are connected to a single electronic board 33 containing the electronics required for signal conditioning (e.g., power supply, amplification, and filtering) and other control requirements for the sensors. A pressure relief valve 380 is provided in the event the pressures inside the collection chamber exceed a critical value. Once the measurements are completed gases are vented through the pump 32. The sensing unit can also include a pressure sensor 323 for detecting the pressure exerted by the pump 32. An internal secondary filter 321 can be provided for use during calibration of the sensing unit, e.g., detecting ambient gas concentrations.

Figure 17:
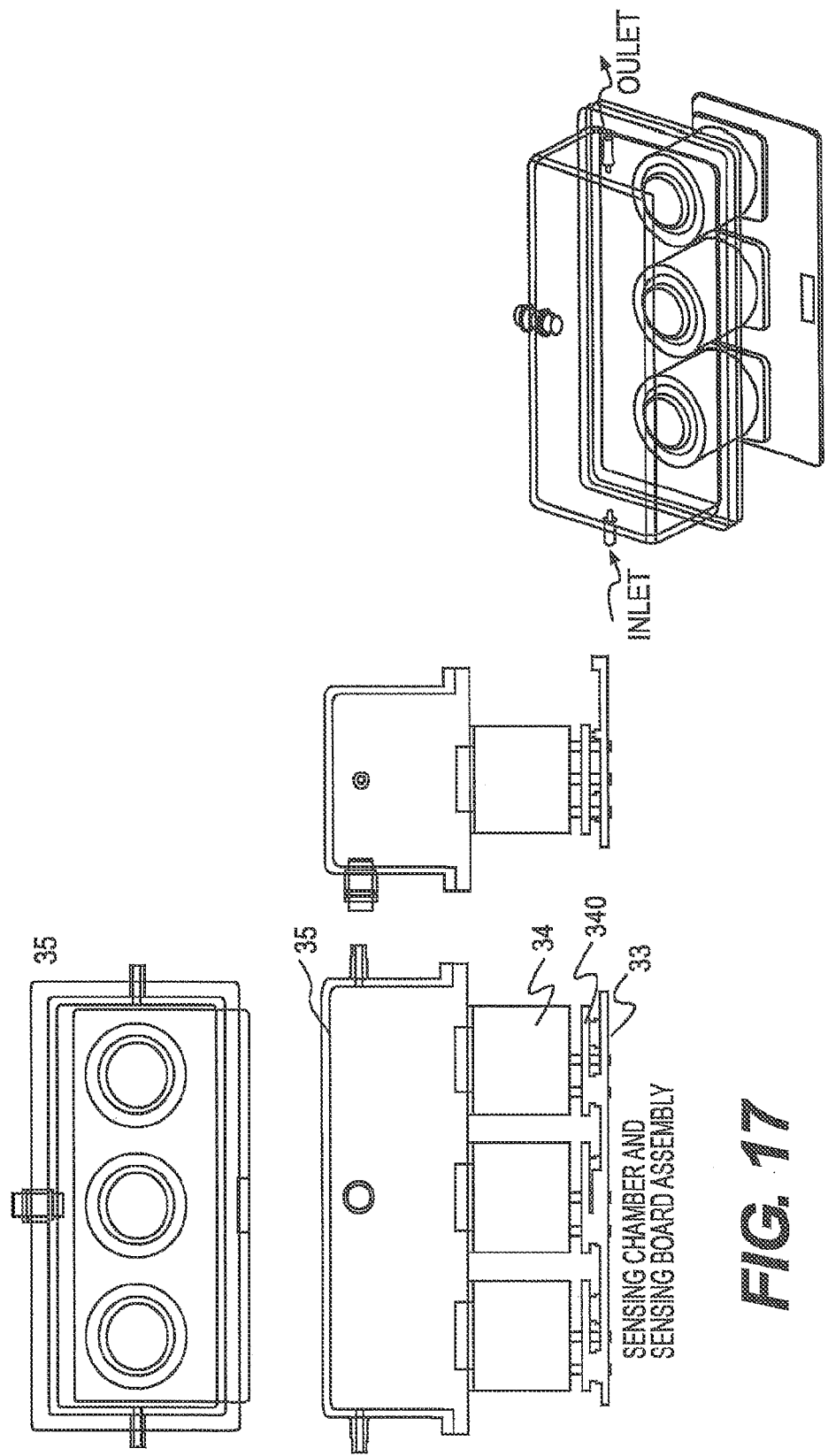
FIG. 17 shows a sensing module as disclosed herein.
Figure 19A:
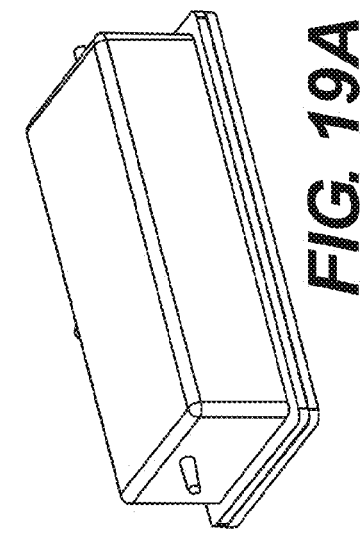
FIG. 19 is an exploded view, perspective view, and cross-sectional view of a sensing chamber assembly as disclosed herein.
Figure 19B:
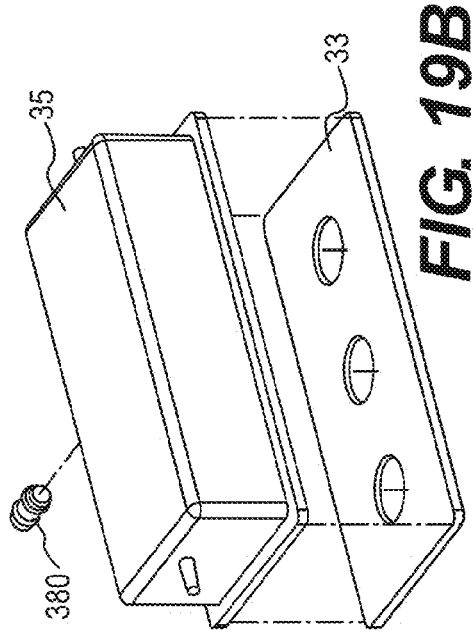
Figure 19E:
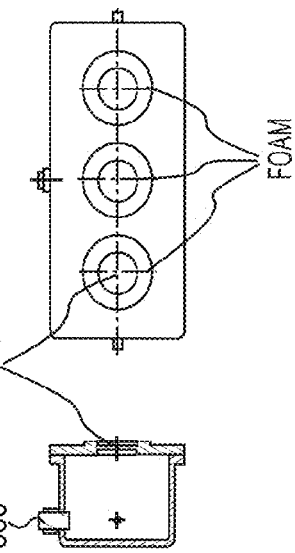
Figure 19C:
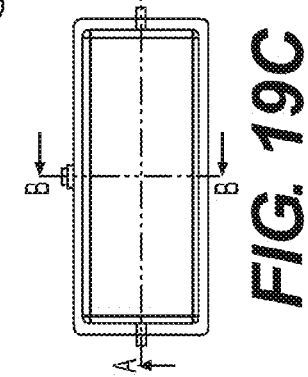
Figure 19D:
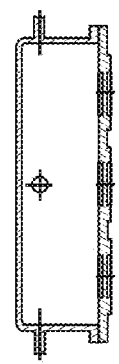

FIG. 17 shows a configuration of the sensing chamber 35 with gas sensors 34, connection base assemblies 340, and sensor board 33 for the system architecture as shown in FIGS. 5 and 6. For simultaneous sensing of the gases, infra-red (IR) sensors are used for $CH_4$ and $CO_2$, and electrochemical sensors are utilized for $H_2$. Unlike semiconductor sensors (for $H_2$) which require heating of the gas, this configuration can utilize simultaneous measurement of all the ppm levels thereby reducing the read time of the entire sensing unit. For sequential sensing, the IR sensors ($CH_4$ and $CO_2$) are triggered first in the order of sensing. The $H_2$ sensor is triggered later in order to avoid interactions between the heat produced by the sensor and the $CH_4/CO_2$ sensors which use IR methods. For example, in sequential sensing, heat produced by a solid state semiconductor-type $H_2$ sensor will not affect the IR sensors for detecting $CH_4$ and $CO_2$.

FIG. 18 depicts the layout of the gas sensors 34, their connection base 340 assemblies, and sensor board 33. FIGS. 19A-19E show perspective, exploded, and cross-sectional views of the sensing chamber 35.

FIGS. 16-19 show a sensing chamber containing three gas sensors. However, the dimensions of the sensing chamber and number and type of sensors contained in each chamber can be changed based on the type of sensor and gas to be detected, as understood by a person of ordinary skill in the art.

Figure 21:
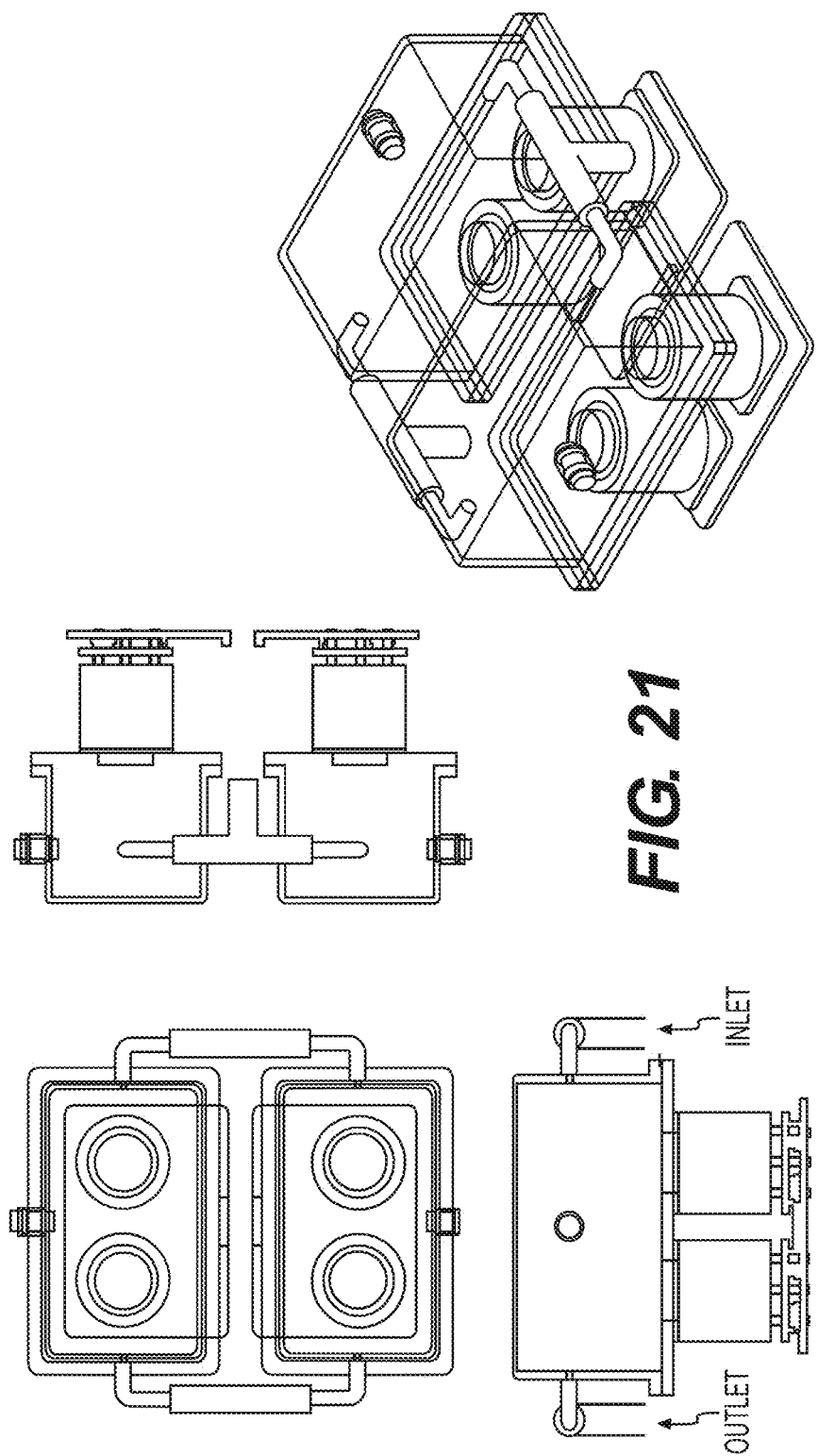
FIG. 21 shows another sensing module as disclosed herein.
Figure 25:
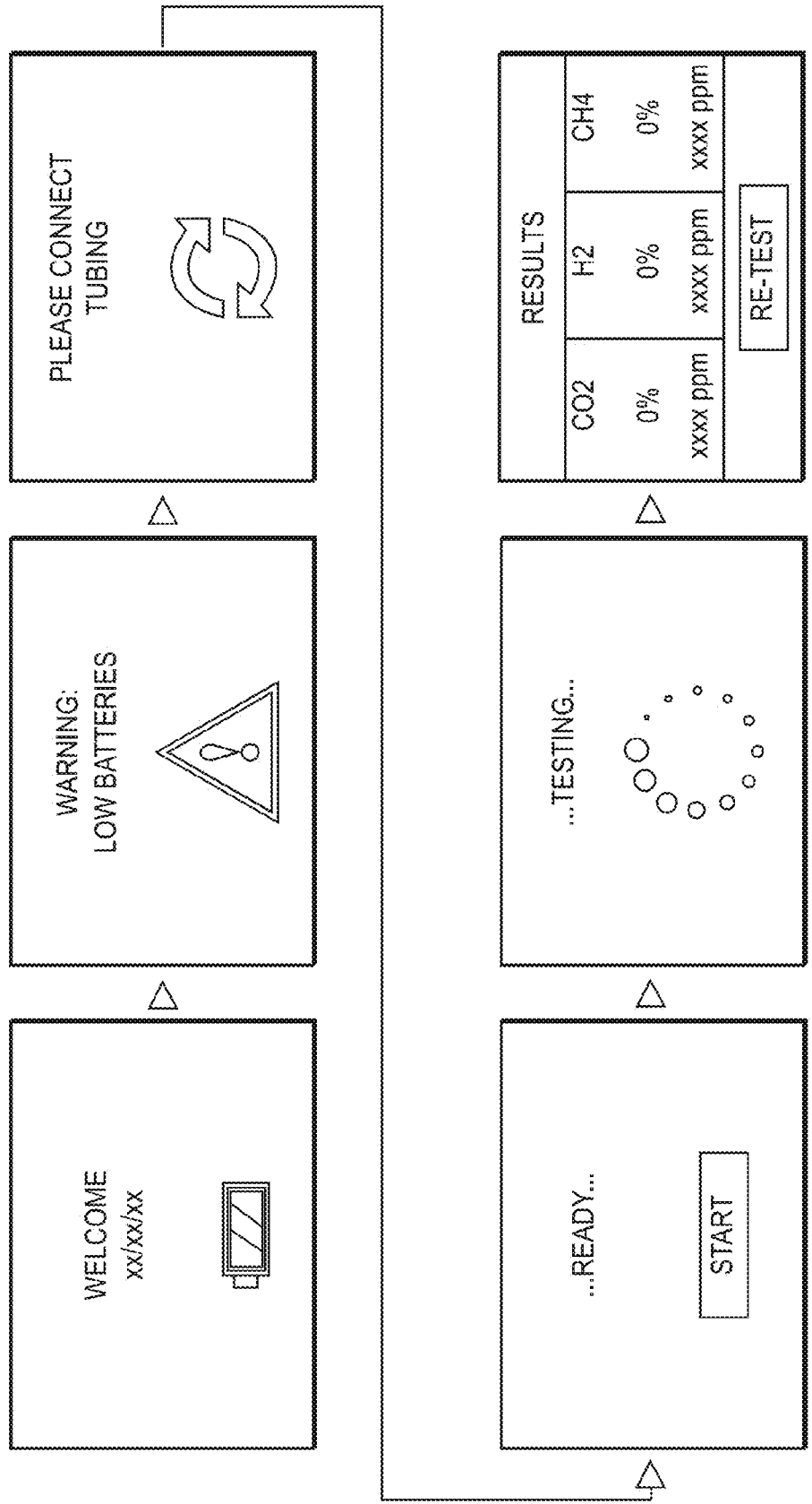
FIG. 25 is a graphical view of a user-screen interface for the devices disclosed herein.

Another configuration for the sensing unit, as shown in FIGS. 20-21, is to utilize two separate sensing chambers 35, for example, one chamber for the IR based $CH_4/CO_2$ sensors, and another chamber for semiconductor sensors, primarily $H_2$, and optionally semiconductor based sensors for $CH_4$ (shown in the figures as four sensor locations). In this configuration, perfect thermal isolation can be achieved by separation of the sensing volumes into two chambers, at the expense of some risk due to splitting of the gas flow stream. The sensing unit can also include a display 36 and battery 39.

Gas ingress can be achieved when the processor (not shown) starts the pump 32 which opens a one-way valve 320 and enables transport of gas through the internal secondary filter 321. Gas passes through the in-series flow sensor 322 and is simultaneously transported to the first sensing chamber and the second sensing chamber as it passes through a connector 37b. The sensors within each chamber can be connected to a single electronic board 33 containing the electronics required for signal conditioning (e.g., power supply, amplification, and filtering) and other control requirements for the sensors. A pressure relief valve 380 can be provided for each chamber in the event the pressures inside the collection chamber exceed a critical value. Once the measurements are completed gases are vented through the pump 32. The sensing unit can also include a pressure sensor 323 for detecting the pressure exerted by the pump 32. An internal secondary filter 321 can be provided for use during calibration of the sensing unit, e.g., detecting ambient gas concentrations.

FIGS. 22A and 22B depict the layout of the gas sensors 34, their connection base 340 assemblies, and sensor board 33 as used in the sensing unit configuration shown in FIGS. 20-21. FIGS. 23A-23E provide perspective, exploded, and cross-sectional views of the sensing chambers 35 of the sensing unit shown in FIGS. 20-21.

FIGS. 20-23 show a sensing chamber containing two gas sensors. However, the dimensions of the sensing chamber and number and type of sensors contained in each chamber can be changed based on the type of sensor and gas to be detected, as understood by a person of ordinary skill in the art.

The pump housed within the sensing unit is designed to be capable of delivering the pressure differentials required to transport gas while avoiding exceeding the liquid breakthrough pressure for the liquid membrane filters used in the tubing. Engineering flow calculations can be conducted to determine the pressure differential required to generate adequate flow of gas and liquid. Using the following flow calculation input parameters, Veress needle lumen of 0.4 mm, Initial length of the tube from Veress needle to filter ~24 mm, tubing OD-12 mm, ID 9 mm, worst case filter parameters (0.2 um pore dia hydrophobic filter, 0.12 mm thick, 0.01 um pore diameter, hydrophilic, 0.12 mm thick, OD 2*tube dia=24 mm.), total tubing length of 8 ft, and an internal (to sensing unit) 0.2 um pore dia hydrophobic filter, 0.12 mm thick, a pressure differential of 0.92 mBar (91.89 N/m$^2$) is required to achieve gas flow, and a differential of 50.99 mBar (5099 N/m$^2$) is required to transport liquid over this distance. Thus, to avoid liquid ingress, a pump capacity of 5 mBar was selected to ensure safe and preferential transport of gas species, when combined with the liquid bypass filter design. Numerous commercial pump suppliers provide pumps in this range of pressure differential capacities (e.g. KNF Inc, Pfeiffer, etc).

For selection of gas sensors, a detailed weighted Pugh Matrix method for each gas was utilized in conjunction with the following metrics, sensing range, warm-up time, operating temperature, response time, accuracy, least count/resolution, sensor life, power consumption, calibration intervals, size, and other sensor compatibility issues. The Pugh matrix results can also be adjusted based on secondary factors such as manufacturing cost, service cost, design time, and parts availability. FIG. 24 identifies acceptable sensor technologies for the present devices and methods. These technologies in various combinations can be utilized for the various system architectures chosen for the sensing unit designs.

The user interface is designed to be an extremely simple sequence to enable a layperson to work with the device/sensing unit. The high level and low level (software level) interactions are designed and depicted in FIGS. 25-28.

At the highest level, i.e., the user-screen interface, the interaction involves tactile engagement with the touch screen display on the front of the hand held unit. This on-screen logic sequence is graphically depicted in FIG. 25 (actual display).

Figure 26:
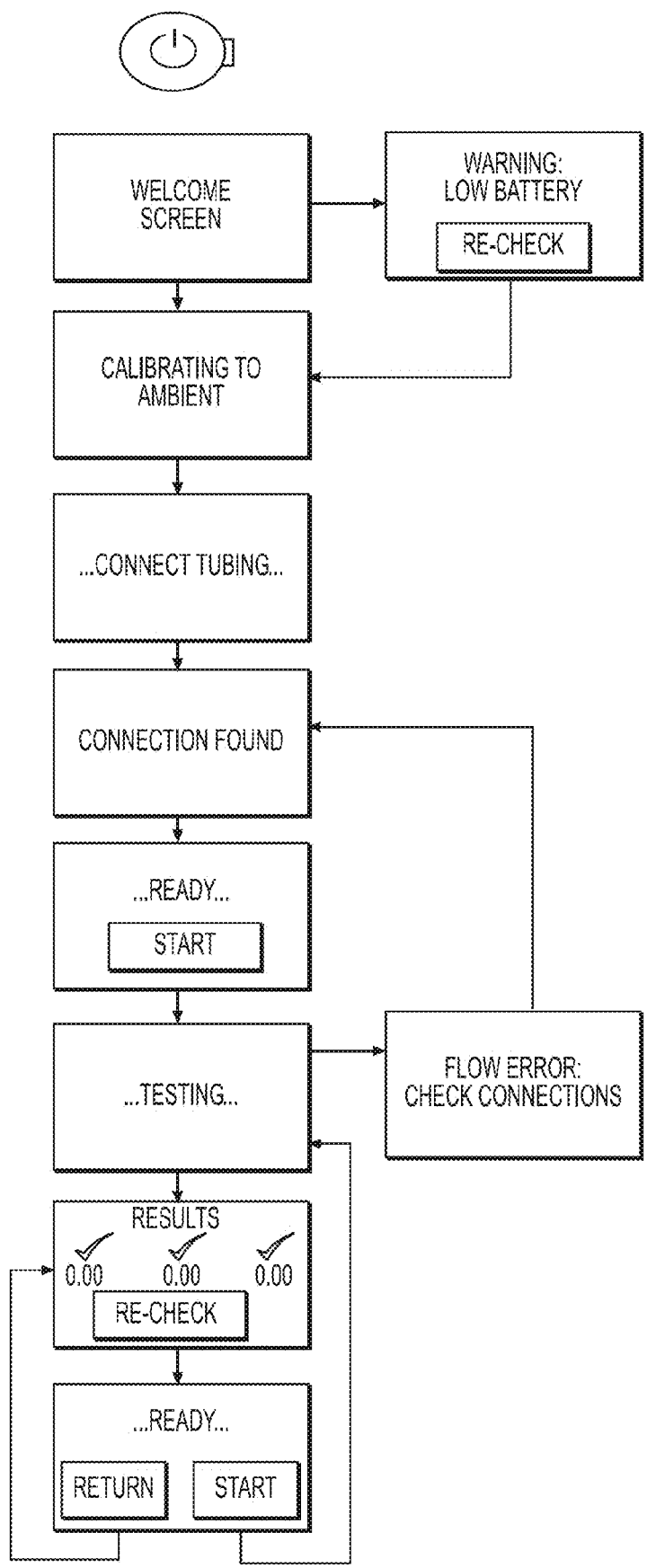
FIG. 26 is a logic-flow of the user interaction for the devices disclosed herein.
Figure 27:
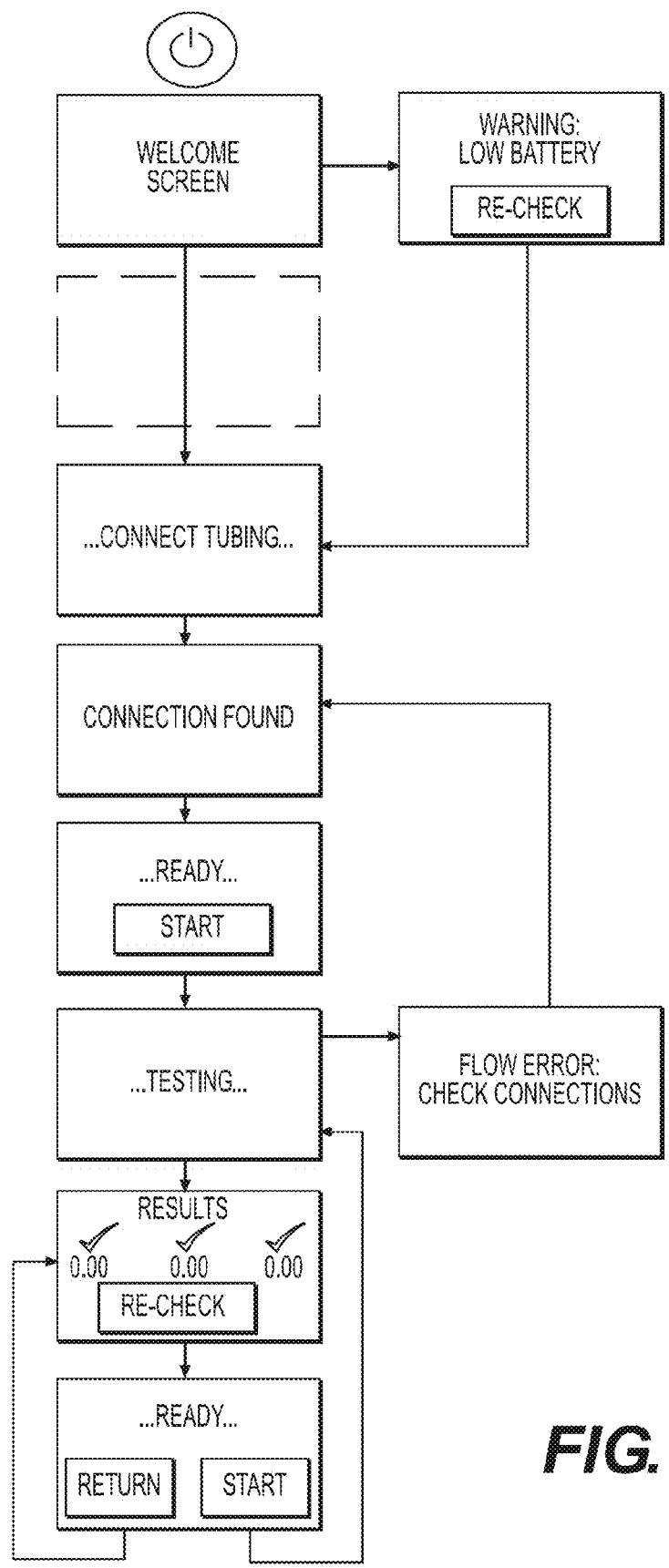
FIG. 27 is another logic-flow of the user interaction for the devices disclosed herein.

The device can make use of two options for the logic flow underlying the high level user interaction (FIG. 26—Option 1 and FIG. 27—Option 2). At this level the user interaction involves the following steps.

Turn on the device
Displays the welcome screen
  A warning is displayed if the battery charge is low (software interrupt requiring low power). Low Battery—Recheck/Recharge
  If battery power is adequate, the software algorithm will proceed to run an internal "Self-Test" to ensure that all the sensors and pump are working within the designed operating parameters.
  If battery power is adequate, screen displays the message "Calibrating to Ambient" (denoting the process of establishing the baseline levels of gases in the environment.)
  Calibration complete (In this option 1, calibration feedback and success is explicitly communicated to the user. In option 2, calibration is a background process and not necessarily communicated.)
Message to user to connect the tubing.
If the tubing is connected correctly this completes the active sensing circuit. Message to user "Connection Found"
Message to user that system is "Ready"
User presses "Start" to initiate gas collection
Message to user "Testing"
If adequate gas is collected based on flow meter monitoring and/or pressure sensors, results are displayed for each of the gases. If not, "Flow error message" with note to check tubing connections.
Retest option displayed for user to run test again.

Figure 28:
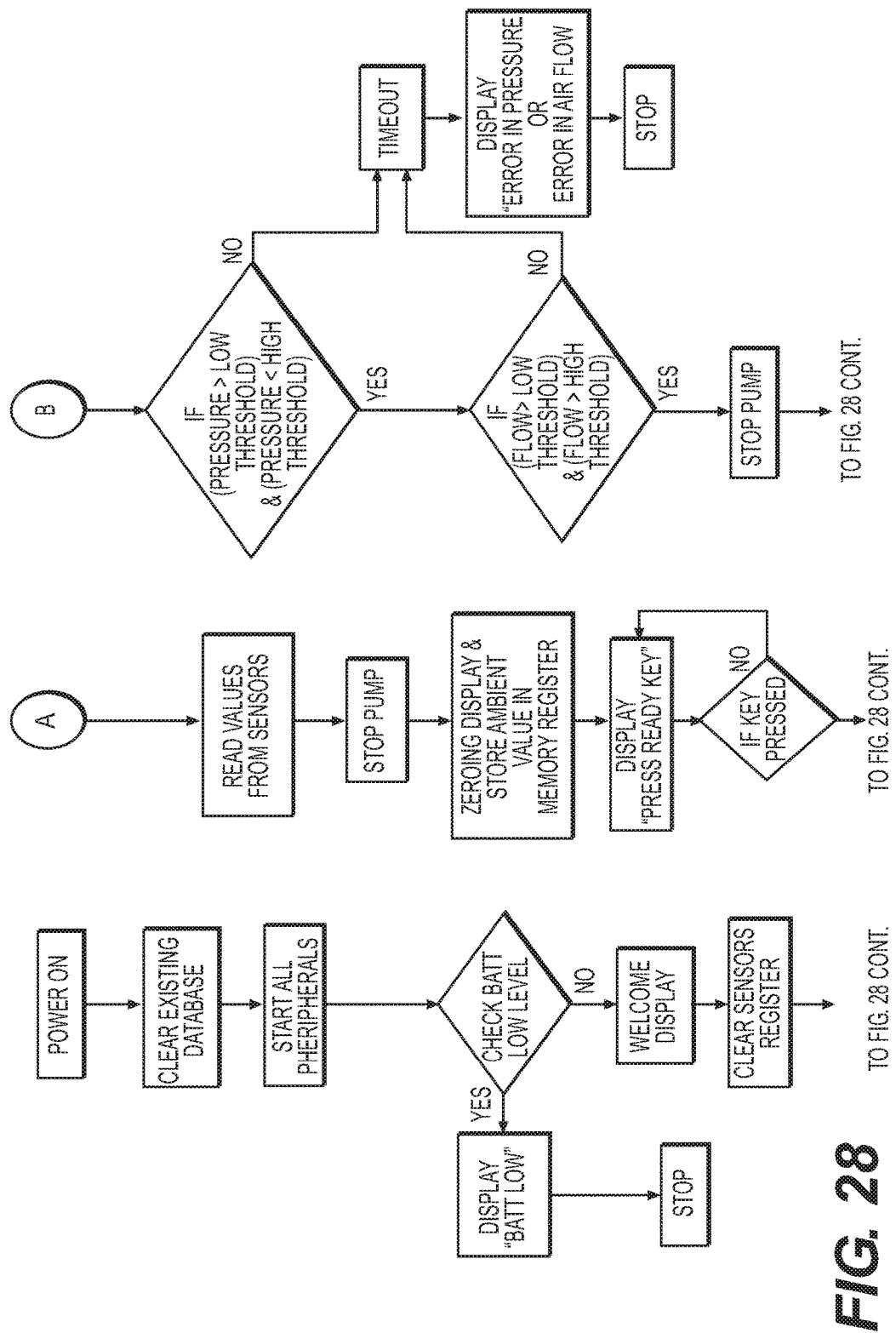
FIG. 28 is an algorithm flow for the devices disclosed herein.
Figure 28:
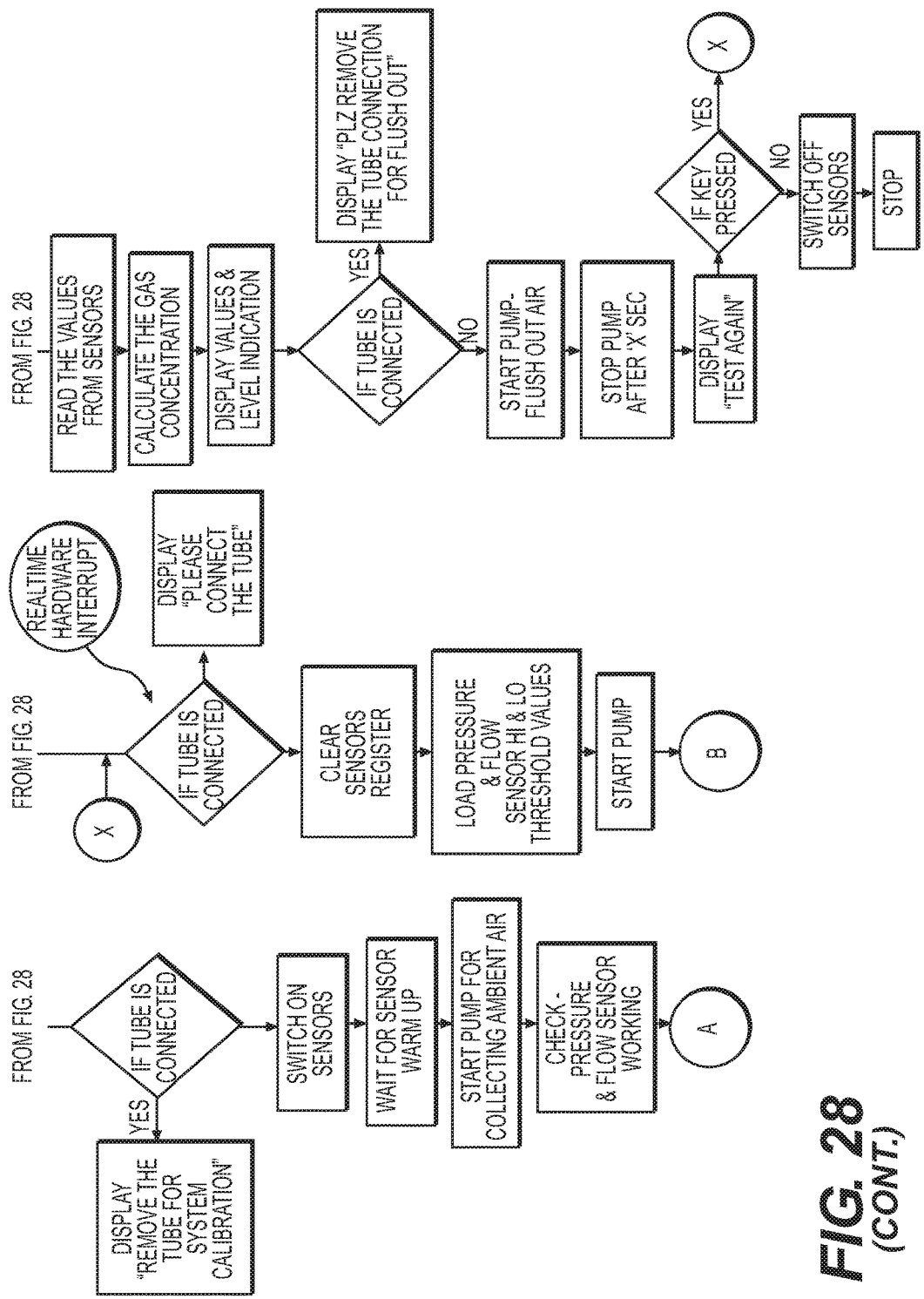

The low level software algorithm is designed to bridge the communication between the user- and device touch screen and the required commands at the digital-analog interface to communicate with the various pieces of hardware in the sensing system. FIG. 28 depicts the preferred software algorithm flow with appropriate checks to address various risks and failure modes potentially encountered in operation of the sensing unit.

The methods and devices disclosed herein can be used during various stages of or continuously throughout laparoscopic surgery. These surgical stages include pre-insufflation, intraprocedure and post-insufflation, and post-abdominal/pelvic procedures.

The pre-insufflation stage of laparoscopic surgery involves blind placement of a Veress needle or trocars into the abdominal or pelvic cavities. During this surgical stage, surgeons insert a hollow needle into the abdomen or, alternately, a trocar through an incision, and must ensure that they do not damage/perforate the bowel. The present methods and devices can be used during this stage to conduct an aspiration and sensing test after placement of the needle/trocar to determine if a bowel perforation injury has occurred.

Intra-procedure and post-insufflation stage refers to the surgical stage during which surgeons conduct the abdominal/pelvic procedure and just prior to closing the patient. Carbon dioxide gas is typically used to insufflate the abdominal cavity, also referred to as creating a pneumoperitoneum. The present detection system can be used to detect for the presence of other gaseous species, including hydrogen, methane, sulfide, and nitrogen, in the abdomen or pelvic cavities via discrete or real-time testing. The device can also be used to detect for elevated concentrations of these gases as compared to a baseline or previously measured level.

The system described herein can be used after completion of abdominal/pelvic procedures. For the example, the present systems and methods can be used to identify bowel perforation injuries in patients who have already undergone surgery and present various symptoms during the post-operative recovery period. In these patients, the presence of perforation and the precise confirmation of the same is extremely important given the major ramifications of such an event which if true results in exploratory surgery, creation of a colostomy and immediate major impact on the quality of life. In addition to this, the patient has to undergo another surgery after resolution of an infection resulting from the perforations, this time to reverse the colostomy. The application of the bowel perforation detection technology can be facilitated via a paracentesis procedure with ultrasound guidance, used to aspirate abdominal gas contents to enable diagnosis of the presence of bowel perforation with a high degree of reliability.

The methods and devices disclosed herein can also be used for repeated sampling and detecting during a surgical procedure. For example, for a laparoscopic surgery, the device can be connected to the medical device inserted into the abdominal cavity prior to insufflation to perform repeated sampling and gas-detecting during the surgery, and disconnected after completion of the procedure and immediately prior to removal of the medical device from the abdominal cavity. The methods and devices can be adapted to sample and detect gas at pre-determined intervals, for example, by programming the device, or can be adapted for on-demand sampling and testing by a user. The timing and number of samples obtained and analyzed can be adapted depending on the type of procedure, for example, laparoscopic surgery or diagnostic procedures, as would be understood by a person of ordinary skill in the art.

The present systems and methods can also be used to detect bowel perforation injuries occurring in other situations, for example, trauma and non-laparoscopic surgeries. For example, the device can be used in conjunction with exploratory aspiration procedures done with paracentesis needles and enable detection of bowel gases in the abdomen.

The bowel perforation detection system can be setup by the operating room staff in a very short period of time with a connections-to-measurement time window of about two minutes or less. However, this does not limit the use of the device by the surgeons over a longer time window if desired by the needs of the physician or the procedure. This is critical because there is very little time available between needle placements and initiation of pneumoperitoneum. As a result of this rapid overall performance envelope for connection-to-measurement, the system incorporates rapid mechanical connections/couplings that can be accomplished by the surgeon, surgeons assistant, and scrub/circulating nurses, a very simple user interface, (involving aspirate-sense-results display steps), software algorithms and gas sensors that work in conjunction to deliver readings on the digital display rapidly to the user.

The bowel perforation detection system can be used in a surgical operating room setting during laparoscopic procedures and includes features that address the unique requirements of the connections with the Veress needle using a tubing coupler, crossing the sterile field to make a connection with a non-sterile sensing unit that is reused across procedures and patients. The sterile end of the tubing is handled by staff that are within the sterile operating field (e.g., surgeon, surgeon's assistant, scrub nurse), while the non-sterile end is handled by the circulating nurse or other assisting staff.

During usage of the system once connected to the Veress needle, the surgeon performs a common clinical maneuver called a Hiss test prior to connecting the system to the needle. The purpose of this test is to ensure that the outside air is entering the abdomen and will do so if the needle tip is indeed in the peritoneal cavity. One of the consequences of this Hiss test is that outside air will mix with any bowel gases (if present) in the abdominal cavity which will dilute the bowel gas concentrations. However, the benefit of the Hiss test is that it will ensure that any trapped bowel gas in various pockets within and between abdominal or pelvic organs will be freed up and available for aspiration. Typically several hundred cc of air is brought into the peritoneal cavity during a hiss test. To accommodate this dilution level, the sensors and software programming can be configured to detect small elevations/changes in gas concentrations above baseline values.

Figure 2:
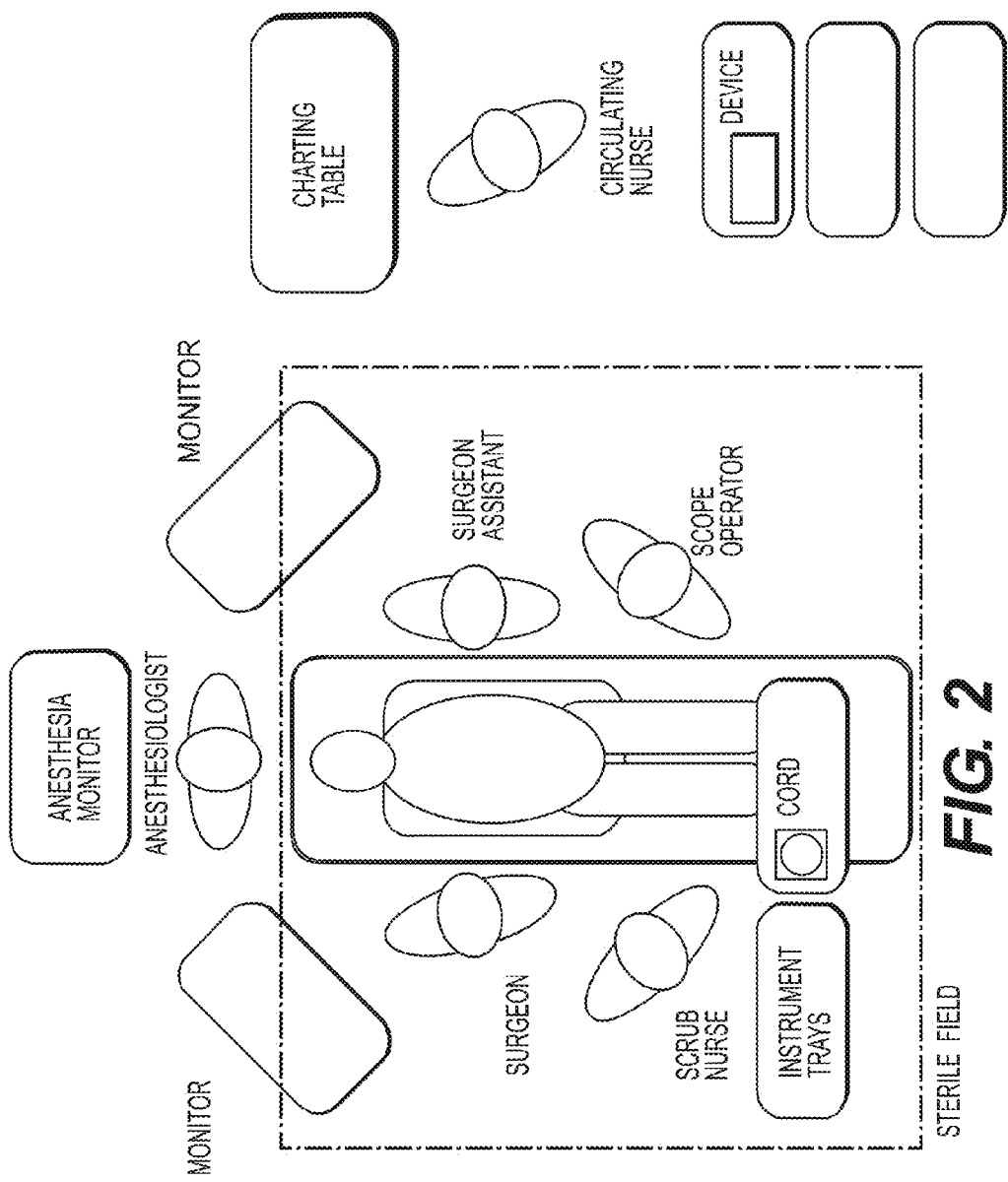
FIG. 2 is an exemplary operating room layout for use with the methods and devices disclosed herein.
Figure 3:
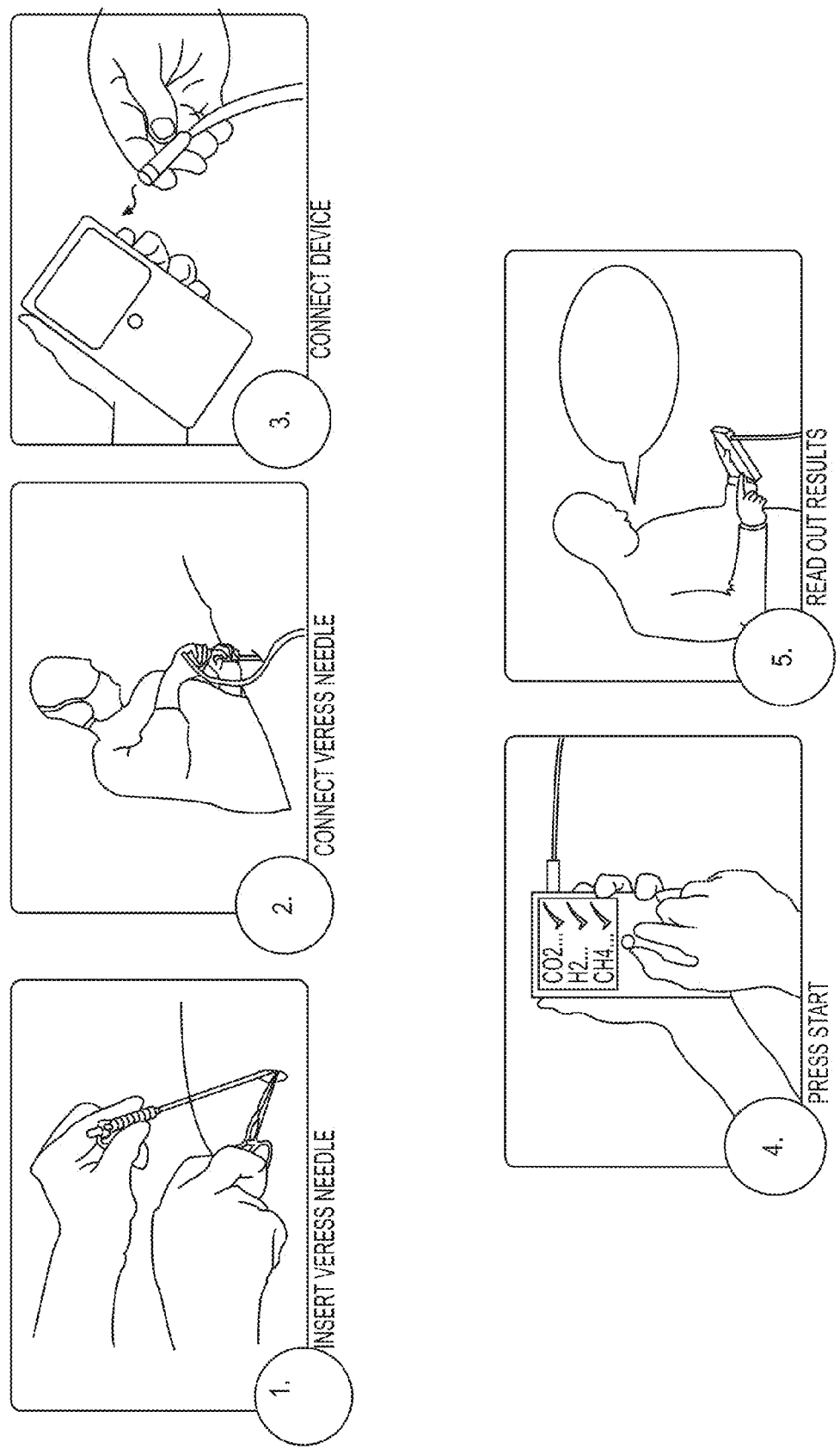
FIG. 3 is a schematic depiction of a bowel perforation detection method as disclosed herein.

The following list provides exemplary steps for possible usage of the present system. Staff within the sterile field can include a Surgeon (S), a Surgeon Assistant (SA), and a Scrub Nurse (SN). Staff outside sterile field can include a Circulating Nurse (CN). FIGS. 2 and 3 provide view of an operating room layout and flowchart of a laparoscopic surgery using the present system. The exemplary steps are as follows:

The device and tubing are prepared on surgical tray for use.

The tubing is sealed in sterile packaging (e.g., double tyvek pack/pouch).

New tubing filter/cartridge is connected to device (the tubing can be packed and—delivered including the Filter which is also a onetime use).

Surgeon (S/SA) performs standard Veress needle insertion (without insufflation of $CO_2$).

Tubing is delivered into sterile field (CN)—standard drop in sterile technique.

Tubing is connected to Veress needle via Luer-Lok connection. Anyone inside the sterile field can execute this connection.

The other end of the tubing is transferred by SN/SA/S to CN.

CN can connect tubing to device/filter via connection.

CN can confirm with staff within the sterile field that a secure connection is made to the Veress needle.

CN can implement/start the device.

CN reads device feedback to decision makers (e.g., S/SA).

S/SA interprets device feedback and determines next step.

Insufflation of $CO_2$ followed by trocar placement is next step if surgery can proceed;

Tubing is disconnected from the Veress needle.

Tubing is disconnected from the system and discarded.

The system filter is removed/replaced device cleaned.

The system is cleaned and retuned to base/docking station.

Alternative step orders or additional steps based on the specific type of procedure can be made. Additionally, surgeons can alter the order of certain steps based on personal preference.

The device can allow surgeons to avoid delay in treating bowel perforation and the complications related to seepage of bowel contents into the abdominal cavity. The device may also be utilized to detect bowel perforation from ruptured diverticulitis or trauma in closed abdomens.

This same device and method may be used as an adjunct to other modalities in detecting these perforations caused by trauma or rupture diverticulitis. The methods and devices described herein can also be used when the abdomen is closed and a perforation is suspected from a ruptured diverticulum or trauma. A 27 gauge needle can be placed through the abdominal wall and connected to the device for a sample of abdominal gases to be analyzed.

EXAMPLES

Example 1

Filter-Tubing Assembly Testing

Figure 29:
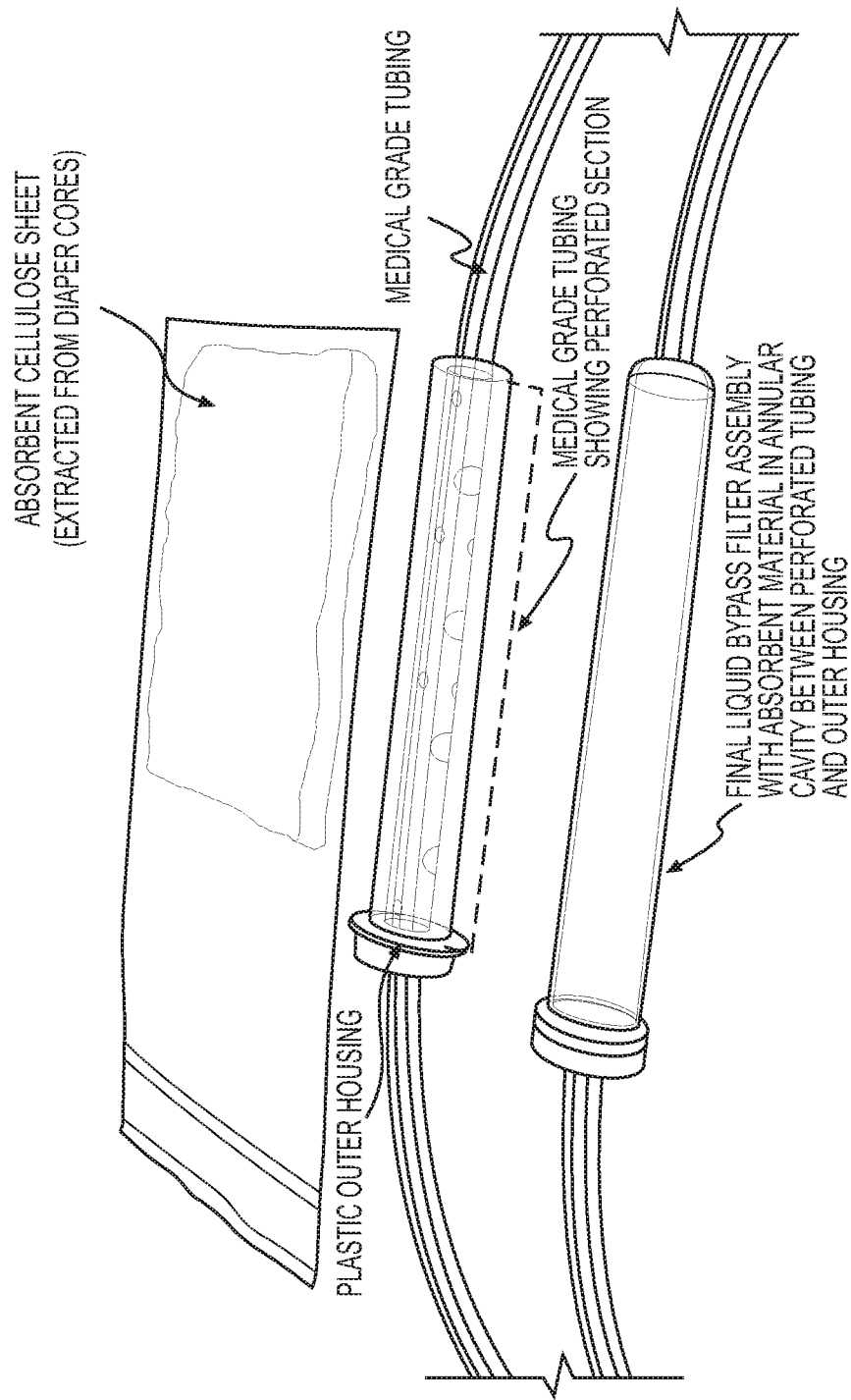
FIG. 29 is a photograph of a bypass filter construction as disclosed herein.
Figure 30:
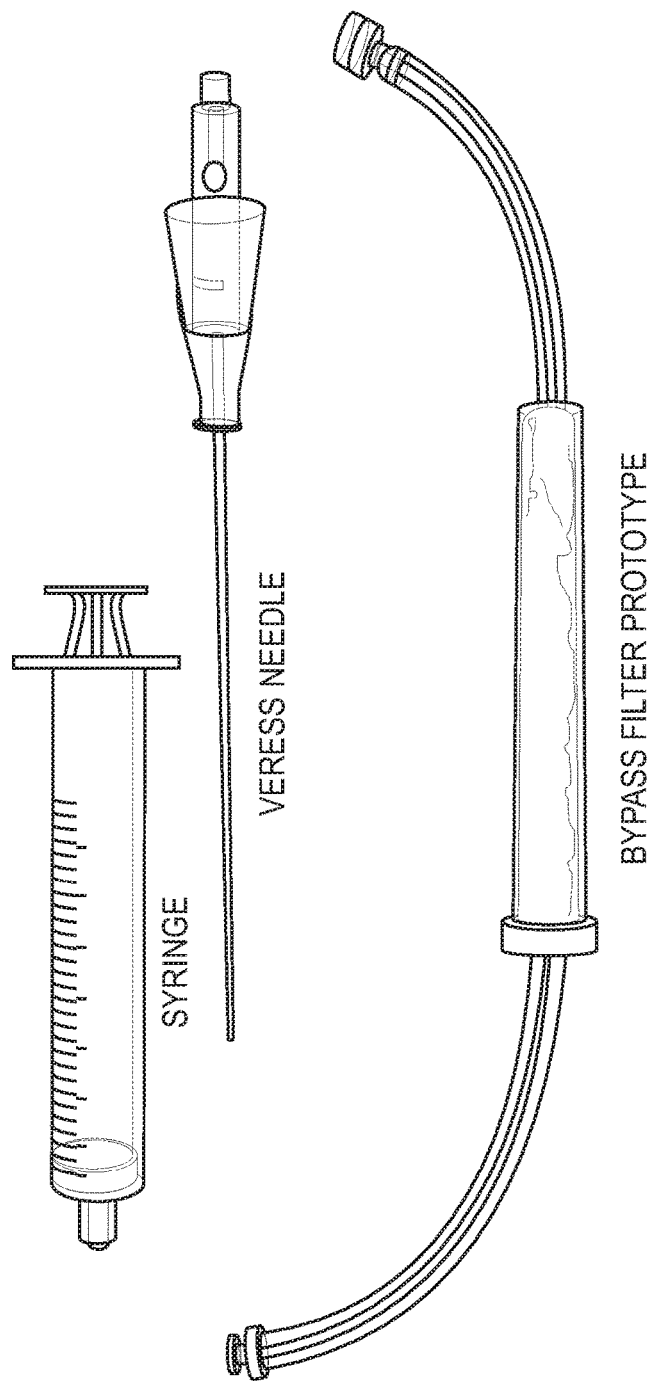
FIG. 30 is a photograph of a bypass filter construction as disclosed herein.

A liquid bypass filter assembly is tested for the ability of the perforated tubing-absorbent sleeve assembly to achieve lateral fluid absorption in order to ensure a viable gas flow lumen. FIG. 29 is a photographic of the materials for use in the test. These include a Veress needle, colored water for visualization, a length of polyurethane medical grade tubing with a perforated section, a sheet of absorbent cellulose non-woven material, a rigid plastic housing, silicone sealant, and a syringe to serve as the pump. As shown in FIG. 30, the prototype bypass filter is constructed by inserting the perforated tube into the clear plastic housing. Following this, the absorbent cellulose wicking material is packed into the annular cavity created between the perforated section and the plastic housing. The ends of the plastic housing are sealed with silicone adhesive to prevent leakage from the annular space.

Figure 31:
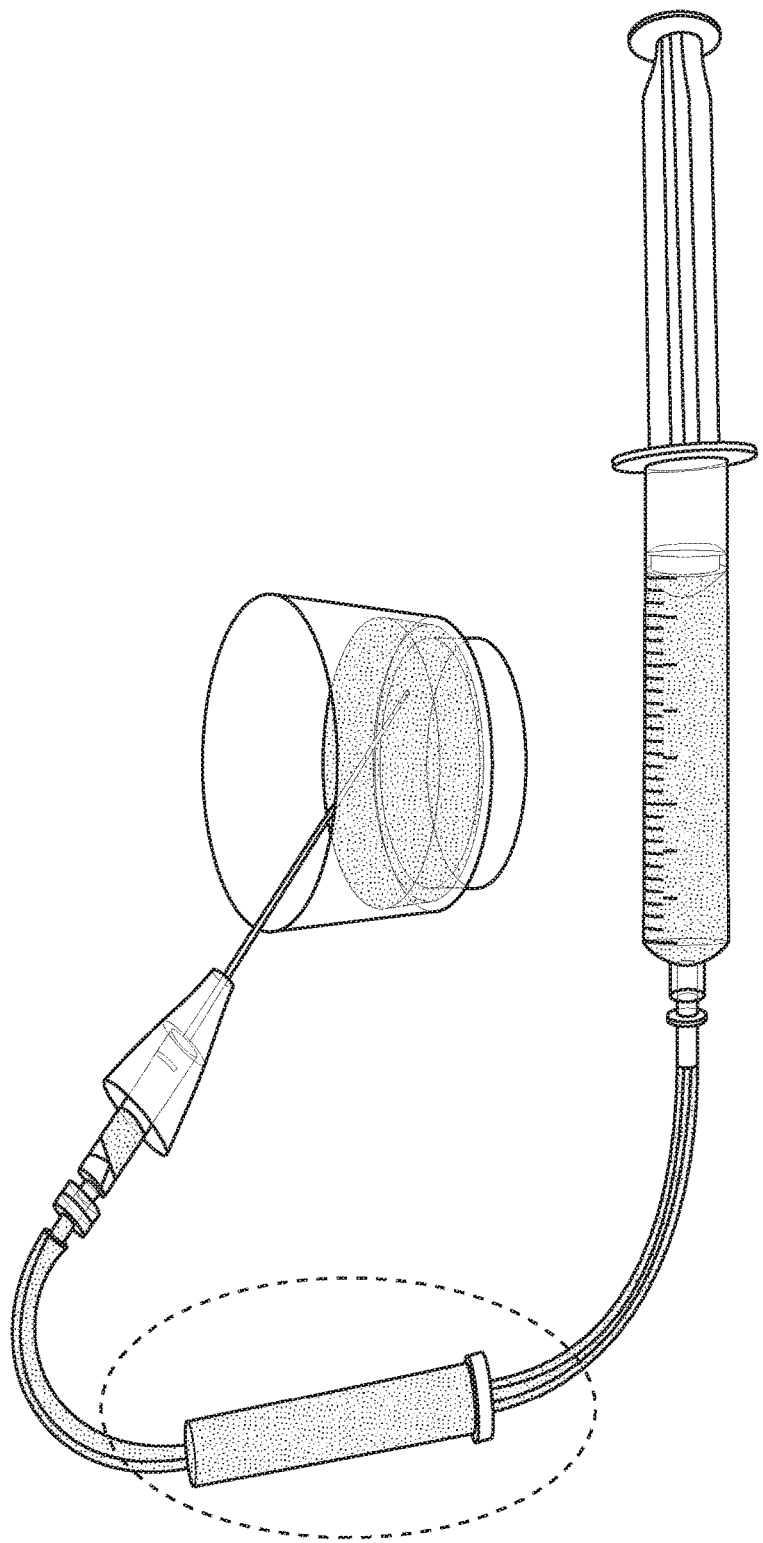
FIG. 31 is a photograph of the wicking function of a bypass filter construction as disclosed herein.

The testing process is shown in FIG. 31. Testing is initiated by connecting the tubing at one end to a Veress needle and the syringe at the other end using standard luer lock connectors (manufactured by Qosina Corporation®).

Following this, suction is applied by drawing back on the syringe plunger to draw fluid through the distal end of the Veress needle, which is positioned in the colored water. As soon as the liquid front reached the absorbent section, it is immediately absorbed laterally into the cellulose sleeve, in the circled area of FIG. 31. Furthermore, even in the absence of a membrane filter, while the fluid is drawn into the syringe, the absorbency of the sleeve is so pronounced that it can wick fluid from the syringe back into the filter assembly. This example demonstrates the engineering functionality of the liquid bypass filter design.

While the foregoing disclosure has been described in some detail for purposes of clarity and understanding, it will be appreciated by one skilled in the art from a reading of this disclosure that various changes in form and detail can be made without departing from the true scope of the disclosure and appended claims.

What is claimed is:

1. A bowel perforation detection device comprising:
    a sample delivery unit comprising: an outer housing section,
    an inner tubing section having a perforated portion with multiple perforations configured to transport an aspirate sample comprising a gas component, a liquid component and a microbial component,
    a sleeve comprising a wicking material disposed between the perforated portion of the inner tubing section and the outer housing, wherein the sleeve and the perforated portion are configured to pass the liquid component of the aspirate sample through the perforated portion to the wicking material,
    a hydrophobic liquid filter having pore sizes ranging from 100 microns to 500 microns configured to filter a residual liquid component from the aspirate sample, a gas and microbial filter configured to filter the microbial component from the aspirate sample, separating the gas component of the aspirate sample for analysis:
    a sensing unit comprising a methane gas sensor, a hydrogen gas sensor, a pump, a processor, and a display; and
    an electrical connector assembly comprising a conducting element configured to connect the sample delivery unit and the sensing unit.

2. The device of claim 1 wherein said gas and microbial filter comprises a hydrophobic filter having minimum pore size of 0.2 microns or a hydrophilic filter having a minimum pore size of 0.01 microns.

3. The device of claim 1 wherein said inner tubing section of the sample delivery unit comprises a one-way valve.

4. The device of claim 1 wherein said methane gas sensor and hydrogen gas sensor are selected from the group consisting of contact gas sensors, non-contact gas sensors, and combinations thereof.

5. The device of claim 1 wherein said sensing unit further comprises a sensor selected from the group consisting of a carbon dioxide gas sensor, a sulfide gas sensor, a nitrogen gas sensor, and combinations thereof.

6. The device of claim 1 wherein said methane gas sensor is an infrared sensor and said hydrogen gas sensor is a solid state sensor.

7. The device of claim 1 wherein said methane gas sensor and hydrogen sensor detect the concentration of gases in real-time.

8. The device of claim 1, wherein said electrical connector assembly comprises a first section comprising the conducting element; and
    a second section comprising a paired pin conductor set, wherein said first section is positioned on the sample delivery unit and said second section is positioned on the sensing unit.

9. The device of claim 1 wherein said display is connected to the sensing unit by a wireless communications system.

10. The device of claim 1 wherein the wicking material comprises a hydrophilic polyurethane foam.

11. The device of claim 1 wherein the wicking material comprises a cellulose fibrous material.

* * * * *